US008731843B2

(12) United States Patent
Halpern et al.

(10) Patent No.: US 8,731,843 B2
(45) Date of Patent: May 20, 2014

(54) OLIGOMER SEQUENCES MAPPING

(75) Inventors: Aaron L. Halpern, San Carlos, CA (US); Igor Nazarenko, Sunnyvale, CA (US)

(73) Assignee: Complete Genomics, Inc., Mountain View, CA (US)

( * ) Notice: Subject to any disclaimer, the term of this patent is extended or adjusted under 35 U.S.C. 154(b) by 349 days.

(21) Appl. No.: 12/698,994

(22) Filed: Feb. 2, 2010

(65) Prior Publication Data

US 2011/0015864 A1    Jan. 20, 2011

Related U.S. Application Data

(60) Provisional application No. 61/149,689, filed on Feb. 3, 2009.

(51) Int. Cl.
*G01N 33/48* (2006.01)
*G06F 19/22* (2011.01)

(52) U.S. Cl.
CPC ..................................... *G06F 19/22* (2013.01)
USPC ........................................................ 702/19

(58) Field of Classification Search
CPC ................................ G06F 19/22; G06F 19/28
See application file for complete search history.

(56) References Cited

U.S. PATENT DOCUMENTS

| | | | |
|---|---|---|---|
| 5,577,249 A | 11/1996 | Califano | |
| 5,795,782 A | 8/1998 | Church et al. | |
| 6,015,714 A | 1/2000 | Baldarellie et al. | |
| 6,055,526 A | 4/2000 | Ambroziak | |
| 6,210,891 B1 | 4/2001 | Nyren et al. | |
| 6,306,597 B1 | 10/2001 | Macevicz | |
| 6,309,824 B1 | 10/2001 | Drmanac | |
| 6,401,043 B1 | 6/2002 | Stanton et al. | |
| 6,401,267 B1 | 6/2002 | Drmanac | |
| 6,403,312 B1 | 6/2002 | Dahiyat et al. | |
| 6,627,067 B1 | 9/2003 | Branton et al. | |
| 6,653,072 B1 | 11/2003 | Patten et al. | |
| 6,775,622 B1 | 8/2004 | Holloway | |
| 6,828,100 B1 | 12/2004 | Ronaghi | |
| 6,833,246 B2 | 12/2004 | Balasubramanian | |
| 6,864,052 B1 | 3/2005 | Drmanac et al. | |
| 6,911,345 B2 | 6/2005 | Quake et al. | |
| 7,058,515 B1 | 6/2006 | Selifonov et al. | |
| 7,238,485 B2 | 7/2007 | Akeson et al. | |
| 7,258,838 B2 | 8/2007 | Li et al. | |
| 7,329,496 B2 | 2/2008 | Dower et al. | |
| 2003/0064382 A1 | 4/2003 | Preparata et al. | |
| 2003/0186226 A1 | 10/2003 | Brennan et al. | |
| 2003/0235854 A1 | 12/2003 | Chan et al. | |
| 2004/0018525 A1 | 1/2004 | Wirtz et al. | |
| 2005/0112590 A1 | 5/2005 | Boom et al. | |
| 2005/0149272 A1 | 7/2005 | Pe'er et al. | |
| 2005/0187916 A1 | 8/2005 | Levin et al. | |
| 2005/0202501 A1 | 9/2005 | Yamamoto et al. | |
| 2006/0073501 A1 | 4/2006 | Van Den Boom et al. | |
| 2006/0286566 A1 | 12/2006 | Lapidus et al. | |
| 2006/0287833 A1 | 12/2006 | Yakhini | |
| 2007/0099208 A1 | 5/2007 | Drmanac et al. | |
| 2007/0122817 A1 | 5/2007 | Church et al. | |
| 2007/0225918 A1 | 9/2007 | Sayood et al. | |
| 2008/0040045 A1 | 2/2008 | Selifonov et al. | |
| 2008/0234136 A1 | 9/2008 | Drmanac et al. | |
| 2008/0256070 A1 | 10/2008 | Inglis | |
| 2008/0279892 A1 | 11/2008 | Jin et al. | |
| 2008/0318795 A1 | 12/2008 | Selifonov et al. | |
| 2009/0029477 A1 | 1/2009 | Meller et al. | |
| 2009/0075343 A1 | 3/2009 | Sparks et al. | |
| 2009/0111115 A1 | 4/2009 | Drmanac et al. | |
| 2009/0111705 A1 | 4/2009 | Sparks et al. | |
| 2009/0111706 A1 | 4/2009 | Sparks et al. | |
| 2009/0264299 A1 | 10/2009 | Drmanac et al. | |

FOREIGN PATENT DOCUMENTS

| | | | |
|---|---|---|---|
| WO | 99/52046 A2 | 10/1999 | |
| WO | WO 2006/073504 A2 | 7/2006 | |
| WO | WO 2007/120208 A2 | 10/2007 | |
| WO | WO 2009/155443 A2 | 12/2009 | |
| WO | WO 2010/091021 A2 | 8/2010 | |
| WO | WO 2010/091023 A2 | 8/2010 | |
| WO | WO 2010/091024 A1 | 8/2010 | |
| WO | WO 2010/127045 A2 | 11/2010 | |

OTHER PUBLICATIONS

International Search Report and Written Opinion corresponding to the PCT application No. PCT/US10/22907, date of mailing Nov. 30, 2010, 9 pages total.

International Search Report and Written Opinion corresponding to the PCT application No. PCT/US10/22912, date of mailing Jun. 23, 2010, 9 pages total.

International Search Report and Written Opinion corresponding to the PCT application No. PCT/US10/32851, date of mailing Nov. 18, 2010, 13 pages total.

Annexstein, "*Generating De Bruijn Sequences: An Efficient Implementation*", IEEE Transactions on Computers, Feb. 1997, (Retrieved from the Internet on Nov. 1, 2010<URL:http://www.computer.org> 46(2):198-200).

Chan et al., "*On the Complexities of de Bruijn Sequences*". Journal of Combinatorial Theory, Series A 1982, 33(3):233-246.

Dahiyat et al., "*De Novo Protein Design: Fully Automated Sequence Selection*", Science 1997, 278 (5335):82-87.

(Continued)

*Primary Examiner* — Anna Skibinsky
(74) *Attorney, Agent, or Firm* — Kilpatrick Townsend & Stockton LLP

(57) ABSTRACT

Mapping oligomer sequences includes receiving a set of related oligomer sequences, applying one or more key patterns derived from a set of oligomer sequence relationships to obtain one or more keys that are consistent with the set of related oligomer sequences, modifying positions within these keys, and locating the one or more keys in an index configured to map a plurality of candidate and/or validated keys to their respective possible and/or validated locations in a reference.

25 Claims, 20 Drawing Sheets

(56) References Cited

OTHER PUBLICATIONS

Flicek et al., "*Sense From Sequence Reads: Methods for Alignment and Assembly*" Nature Methods Supplement Oct. 15, 2009, 6(11S):S6-S12.

Gonnet et al., "*Exhaustive Matching of the Entire Protein Sequence Database*", Science 1992, 256(5062):1443-1445.

Han al el., "*SPIDER: Software for Protein Identification From Sequence Tags With De Novo Sequencing Error*", 2004 IEEE Computational Systems Bioinformatics Conference 2004. (Retrieved from the Internet on Nov. 1, 2010: <URL: http://citeseerx.ist.psu.edu/viewdoc/download?doi=10.1.1.71.8935&rep=rep1&type=pdf>) p. 1-18.

Margulies et al, "*Genome Sequencing in Microfabricated High-Density Picolitre Reactors*"; Nature 2005, 437:376-380.

Ning at al., "*SSAHA: A Fast Search Method for Large DNA Databases*", pp. 1725-1729, Genome Research 2001, 11(10):1725-1729.

Pevzner et al. "*An Eulerian Path Approach to DNA Fragment Assembly*", Proceedings of the National Academy of Sciences 2001, 98(17):9748-9753.

Ronaghi et al., "*Real-Time DNA Sequencing Using Detection of Pyrophosphate Release*", Anal. Biochem, 1996, 242:84-89.

Webb et al. "*BALSA: Bayesian Algorithm for Local Sequence Alignment*" Nucleic Acids Research 2002, 30(5):1268-1277; p. 1269-1272.

Zerbino et al. "*Velvet: Algorithms for De Novo Short Read Assembly Using De Bruijn Graphs*", Genome Research 2008, 18(5):821-829; p. 821-822, 825.

PCT International Search Report and Written Opinion of the International Searching Authority, issued Mar. 16, 2010, application No. PCT/US2010/022913.

Venter, et al., "The Sequence of the Human Genome," Science, 2001, vol. 291, pp. 1304-1351.

Office Action mailed May 23, 2013 in U.S. Appl. No. 12/698,986, 11 pages.

Jiang, Hui, et al., "SeqMap: mapping massive amount of oligonucleotides to the genome," Bioinformatics, 2008, vol. 24, No. 20, pp. 2395-2396.

Li, Ruidang, et al., "SOAP: short oligonudeotide alignment program," Bioinformatics, 2008, vol. 24, No. 5, pp. 713-714.

Li, Heng, et al., "Mapping short DNA sequencing reads and calling variants using mapping quality scores," Genome Research, Aug. 19, 2008, pp. 1851-1858.

European Search Report mailed Dec. 9, 2013 in European Patent Application No. 10739024.7, 10 pages.

| Key | Location |
|---|---|
| AAAAAAA AAAAAA AAAA | Chr2: 10991917 |
| AAAAAA AAAAAA AAAA | Chr7:4534161 |
| AAAAAA AAAAAA AAAC | Chr5: 1121222 |
| AAAAAAAAAAAAAAAG | Chr3: 4352556 |
| ... | ... |
| TCTAGCCATGTGGAA | Chr1: 5312526 |
| ... | ... |
| TTTTAGCCGTGTGGCA | Chr1: 5312525 |
| ... | ... |

FIG. 4A

SEQUENCE LISTING

```
<160> NUMBER OF SEQ ID NOS: 259

<210> SEQ ID NO 1
<211> LENGTH: 10
<212> TYPE: DNA
<213> ORGANISM: HOMO SAPIENS

<400> SEQUENCE: 1
ttcattagcc                                                          10

<210> SEQ ID NO 2
<211> LENGTH: 11
<212> TYPE: DNA
<213> ORGANISM: HOMO SAPIENS

<400> SEQUENCE: 2
gtgtgggtca a                                                        11

<210> SEQ ID NO 3
<211> LENGTH: 11
<212> TYPE: DNA
<213> ORGANISM: HOMO SAPIENS

<400> SEQUENCE: 3
attcattagc c                                                        11

<210> SEQ ID NO 4
```

```
<211> LENGTH: 12
<212> TYPE: DNA
<213> ORGANISM: HOMO SAPIENS

<400> SEQUENCE: 4
tattcattag cc                                                          12

<210> SEQ ID NO 5
<211> LENGTH: 10
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: n = a, c, g, or t

<400> SEQUENCE: 5
gtgtgggtca                                                             10

<210> SEQ ID NO 6
<211> LENGTH: 12
<212> TYPE: DNA
<213> ORGANISM: Homo sapiens

<400> SEQUENCE: 6
gtgtgggtca ag                                                          12

<210> SEQ ID NO 7
<211> LENGTH: 32
<212> TYPE: DNA
<213> ORGANISM: HOMO SAPIENS

<400> SEQUENCE: 7
tgctattcat tagccaagtg tgggtcaagg ta                                    32

<210> SEQ ID NO 8
<211> LENGTH: 16
<212> TYPE: DNA
<213> ORGANISM: HOMO SAPIENS
<220> FEATURE:
<221> NAME/KEY: misc_feature
<222> LOCATION: (14)..(14)
<223> OTHER INFORMATION: w = a or t

<400> SEQUENCE: 8
ttttagccgt gtggca                                                      16

<210> SEQ ID NO 9
<211> LENGTH: 16
<212> TYPE: DNA
<213> ORGANISM: HOMO SAPIENS

<400> SEQUENCE: 9
tagccatgtg ggtcaa                                                      16

<210> SEQ ID NO 10
<211> LENGTH: 16
<212> TYPE: DNA
<213> ORGANISM: HOMO SAPIENS

<400> SEQUENCE: 10
tattagccgt gtggca                                                      16

<210> SEQ ID NO 11
<211> LENGTH: 16
<212> TYPE: DNA
```

```
<213> ORGANISM: HOMO SAPIENS
<220> FEATURE:
<221> NAME/KEY: misc_feature
<222> LOCATION: (2)..(2)
<223> OTHER INFORMATION: w = a or t

<400> SEQUENCE: 11
tctagccatg tgggaa                                                    16

<210> SEQ ID NO 12
<211> LENGTH: 16
<212> TYPE: DNA
<213> ORGANISM: HOMO SAPIENS

<400> SEQUENCE: 12
tagccatgtg ggtcaa                                                    16

<210> SEQ ID NO 13
<211> LENGTH: 20
<212> TYPE: DNA
<213> ORGANISM: HOMO SAPIENS

<400> SEQUENCE: 13
ttagccgtgt ggttcacagt                                                20

<210> SEQ ID NO 14
<211> LENGTH: 20
<212> TYPE: DNA
<213> ORGANISM: HOMO SAPIENS

<400> SEQUENCE: 14
ttagccgtgt ggttcacagt                                                20

<210> SEQ ID NO 15
<211> LENGTH: 10
<212> TYPE: DNA
<213> ORGANISM: HOMO SAPIENS

<400> SEQUENCE: 15
ttcattagcc                                                           10

<210> SEQ ID NO 16
<211> LENGTH: 11
<212> TYPE: DNA
<213> ORGANISM: HOMO SAPIENS
<220> FEATURE:
<221> NAME/KEY: misc_feature
<222> LOCATION: (14)..(14)
<223> OTHER INFORMATION: n is a, c, g, or t

<400> SEQUENCE: 16
gtgtgggtca a                                                         11

<210> SEQ ID NO 17
<211> LENGTH: 11
<212> TYPE: DNA
<213> ORGANISM: HOMO SAPIENS
<220> FEATURE:
<221> NAME/KEY: misc_feature
<222> LOCATION: (14)..(14)
<223> OTHER INFORMATION: n = a, t, c, or g

<400> SEQUENCE: 17
attcattagc c                                                         11

<210> SEQ ID NO 18
```

```
<211> LENGTH: 12
<212> TYPE: DNA
<213> ORGANISM: HOMO SAPIENS

<400> SEQUENCE: 18
tattcattag cc                                                              12

<210> SEQ ID NO 19
<211> LENGTH: 10
<212> TYPE: DNA
<213> ORGANISM: HOMO SAPIENS

<400> SEQUENCE: 19
gtgtgggtca                                                                 10

<210> SEQ ID NO 20
<211> LENGTH: 13
<212> TYPE: DNA
<213> ORGANISM: HOMO SAPIENS

<400> SEQUENCE: 20
gtgtgggtca aag                                                             13

<210> SEQ ID NO 21
<211> LENGTH: 14
<212> TYPE: DNA
<213> ORGANISM: HOMO SAPIENS

<400> SEQUENCE: 21
tttagccgtg tgga                                                            14

<210> SEQ ID NO 22
<211> LENGTH: 16
<212> TYPE: DNA
<213> ORGANISM: HOMO SAPIENS

<400> SEQUENCE: 22
aaaaaaaaaa aaaaaa                                                          16

<210> SEQ ID NO 23
<211> LENGTH: 16
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n = a, t, c, or g
<220> FEATURE:
<221> NAME/KEY: misc_feature
<222> LOCATION: (17)..(17)
<223> OTHER INFORMATION: n = a, t, c, or g

<400> SEQUENCE: 23
aaaaaaaaaa aaaaac                                                          16

<210> SEQ ID NO 24
<211> LENGTH: 16
<212> TYPE: DNA
<213> ORGANISM: HOMO SAPIENS
<220> FEATURE:
<221> NAME/KEY: misc_feature
<222> LOCATION: (16)..(17)
<223> OTHER INFORMATION: n = a, t, c, or g

<400> SEQUENCE: 24
aaaaaaaaaa aaaaag                                                          16
```

```
<210> SEQ ID NO 25
<211> LENGTH: 16
<212> TYPE: DNA
<213> ORGANISM: HOMO SAPIENS

<400> SEQUENCE: 25
tctagccatg tgggaa                                                     16

<210> SEQ ID NO 26
<211> LENGTH: 12
<212> TYPE: DNA
<213> ORGANISM: HOMO SAPIENS

<400> SEQUENCE: 26
aaaaaaaaaa at                                                         12

<210> SEQ ID NO 27
<211> LENGTH: 12
<212> TYPE: DNA
<213> ORGANISM: HOMO SAPIENS

<400> SEQUENCE: 27
aaaaaaaaaa ca                                                         12

<210> SEQ ID NO 28
<211> LENGTH: 12
<212> TYPE: DNA
<213> ORGANISM: HOMO SAPIENS

<400> SEQUENCE: 28
ttagccgtgt gg                                                         12

<210> SEQ ID NO 29
<211> LENGTH: 12
<212> TYPE: DNA
<213> ORGANISM: HOMO SAPIENS

<400> SEQUENCE: 29
tttttttttt tt                                                         12

<210> SEQ ID NO 30
<211> LENGTH: 10
<212> TYPE: DNA
<213> ORGANISM: HOMO SAPIENS

<400> SEQUENCE: 30 ctattyagcc                                                            10

<210> SEQ ID NO 31
<211> LENGTH: 11
<212> TYPE: DNA
<213> ORGANISM: HOMO SAPIENS

<400> SEQUENCE: 31
ctattytagc c                                                          11

<210> SEQ ID NO 32
<211> LENGTH: 12
<212> TYPE: DNA
<213> ORGANISM: HOMO SAPIENS

<400> SEQUENCE: 32
ctattcttag cc                                                         12
```

```
<210> SEQ ID NO 33
<211> LENGTH: 10
<212> TYPE: DNA
<213> ORGANISM: HOMO SAPIENS

<400> SEQUENCE: 33
ttcattagcc                                                          10

<210> SEQ ID NO 34
<211> LENGTH: 16
<212> TYPE: DNA
<213> ORGANISM: HOMO SAPIENS

<400> SEQUENCE: 34
twttagccgt gtggca                                                   16

<210> SEQ ID NO 35
<211> LENGTH: 16
<212> TYPE: DNA
<213> ORGANISM: HOMO SAPIENS

<400> SEQUENCE: 35
ttagccgtgt ggtwca                                                   16

<210> SEQ ID NO 36
<211> LENGTH: 16
<212> TYPE: DNA
<213> ORGANISM: HOMO SAPIENS

<400> SEQUENCE: 36
ttagccgtgt ggttca                                                   16

<210> SEQ ID NO 37
<211> LENGTH: 16
<212> TYPE: DNA
<213> ORGANISM: HOMO SAPIENS

<400> SEQUENCE: 37
ttagccgtgt ggtaca                                                   16

<210> SEQ ID NO 38
<211> LENGTH: 10
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: n is a, c, g, or t

<400> SEQUENCE: 38 tncattagcc                                                          10

<210> SEQ ID NO 39
<211> LENGTH: 11
<212> TYPE: DNA
<213> ORGANISM: HOMO SAPIENS
<220> FEATURE:
<221> NAME/KEY: misc_feature
<222> LOCATION: (3)..(3)
<223> OTHER INFORMATION: n is a, c, g, or t

<400> SEQUENCE: 39
atncattagc c                                                        11

<210> SEQ ID NO 40
```

```
<211> LENGTH: 12
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n is a, c, g, or t

<400> SEQUENCE: 40
tatncattag cc                                                               12

<210> SEQ ID NO 41
<211> LENGTH: 16
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: n is a, c, g, or t

<400> SEQUENCE: 41
tnttagccgt ggtaca                                                           16

<210> SEQ ID NO 42
<211> LENGTH: 16
<212> TYPE: DNA
<213> ORGANISM: HOMO SAPIENS

<400> SEQUENCE: 42
tgttagccgt ggtaca                                                           16

<210> SEQ ID NO 43
<211> LENGTH: 16
<212> TYPE: DNA
<213> ORGANISM: HOMO SAPIENS

<400> SEQUENCE: 43
tattagccgt ggtaca                                                           16

<210> SEQ ID NO 44
<211> LENGTH: 16
<212> TYPE: DNA
<213> ORGANISM: HOMO SAPIENS

<400> SEQUENCE: 44
ttttagccgt ggtaca                                                           16

<210> SEQ ID NO 45
<211> LENGTH: 16
<212> TYPE: DNA
<213> ORGANISM: HOMO SAPIENS

<400> SEQUENCE: 45
tcttagccgt ggtaca                                                           16

<210> SEQ ID NO 46
<211> LENGTH: 16
<212> TYPE: DNA
<213> ORGANISM: HOMO SAPIENS

<400> SEQUENCE: 46
ttagccgtgt ggtgca                                                           16

<210> SEQ ID NO 47
<211> LENGTH: 16
<212> TYPE: DNA
```

```
<213> ORGANISM: HOMO SAPIENS

<400> SEQUENCE: 47
ttagccgtgt ggtcca                                                    16

<210> SEQ ID NO 48
<211> LENGTH: 16
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: n is a, c, g, or t

<400> SEQUENCE: 48
tnttagccgt gtggca                                                    16

<210> SEQ ID NO 49
<211> LENGTH: 16
<212> TYPE: DNA
<213> ORGANISM: HOMO SAPIENS

<400> SEQUENCE: 49
tgttagccgt gtggca                                                    16

<210> SEQ ID NO 50
<211> LENGTH: 16
<212> TYPE: DNA
<213> ORGANISM: HOMO SAPIENS

<400> SEQUENCE: 50
tcttagccgt gtggca                                                    16

<210> SEQ ID NO 51
<211> LENGTH: 15
<212> TYPE: DNA
<213> ORGANISM: HOMO SAPIENS

<400> SEQUENCE: 51
tttagccgtg tggca                                                     15

<210> SEQ ID NO 52
<211> LENGTH: 16
<212> TYPE: DNA
<213> ORGANISM: HOMO SAPIENS

<400> SEQUENCE: 52
ttagccgtgt ggttca                                                    16

<210> SEQ ID NO 53
<211> LENGTH: 16
<212> TYPE: DNA
<213> ORGANISM: HOMO SAPIENS

<400> SEQUENCE: 53
ttagccgtgt ggtcca                                                    16

<210> SEQ ID NO 54
<211> LENGTH: 15
<212> TYPE: DNA
<213> ORGANISM: HOMO SAPIENS

<400> SEQUENCE: 54
ttagccgtgt ggtca                                                     15
```

```
<210> SEQ ID NO 55
<211> LENGTH: 10
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n is a, c, g, or t

<400> SEQUENCE: 55 ttcnttagcc                                                              10

<210> SEQ ID NO 56
<211> LENGTH: 11
<212> TYPE: DNA
<213> ORGANISM: HOMO SAPIENS
<220> FEATURE:
<221> NAME/KEY: misc_feature
<222> LOCATION: (7)..(7)
<223> OTHER INFORMATION: n is a, c, g, or t

<400> SEQUENCE: 56
gtgtggntca a                                                            11

<210> SEQ ID NO 57
<211> LENGTH: 11
<212> TYPE: DNA
<213> ORGANISM: HOMO SAPIENS
<220> FEATURE:
<221> NAME/KEY: misc_feature
<222> LOCATION: (5)..(5)
<223> OTHER INFORMATION: n is a, c, g, or t

<400> SEQUENCE: 57
attcnttagc c                                                            11

<210> SEQ ID NO 58
<211> LENGTH: 12
<212> TYPE: DNA
<213> ORGANISM: HOMO SAPIENS
<220> FEATURE:
<221> NAME/KEY: misc_feature
<222> LOCATION: (7)..(7)
<223> OTHER INFORMATION: n is a, c, g, or t

<400> SEQUENCE: 58
gtgtggntca ag                                                           12

<210> SEQ ID NO 59
<211> LENGTH: 20
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 59
ttcnttagcc gtgtggntca                                                   20

<210> SEQ ID NO 60
<211> LENGTH: 20
<212> TYPE: DNA
<213> ORGANISM: HOMO SAPIENS
<220> FEATURE:
```

```
<221> NAME/KEY: misc_feature
<222> LOCATION: (16)..(17)
<223> OTHER INFORMATION: n is a, c, g, or t

<400> SEQUENCE: 60
ttagccgtgt ggttcnntca                                                     20

<210> SEQ ID NO 61
<211> LENGTH: 20
<212> TYPE: DNA
<213> ORGANISM: HOMO SAPIENS

<400> SEQUENCE: 61
ttcgttagcc gtgtgggtca                                                     20

<210> SEQ ID NO 62
<211> LENGTH: 20
<212> TYPE: DNA
<213> ORGANISM: HOMO SAPIENS

<400> SEQUENCE: 62
ttcgttagcc gtgtggatca                                                     20

<210> SEQ ID NO 63
<211> LENGTH: 20
<212> TYPE: DNA
<213> ORGANISM: HOMO SAPIENS

<400> SEQUENCE: 63
ttcgttagcc gtgtggttca                                                     20

<210> SEQ ID NO 64
<211> LENGTH: 20
<212> TYPE: DNA
<213> ORGANISM: HOMO SAPIENS

<400> SEQUENCE: 64
ttcgttagcc gtgtggctca                                                     20

<210> SEQ ID NO 65
<211> LENGTH: 20
<212> TYPE: DNA
<213> ORGANISM: HOMO SAPIENS

<400> SEQUENCE: 65
ttcattagcc gtgtgggtca                                                     20

<210> SEQ ID NO 66
<211> LENGTH: 20
<212> TYPE: DNA
<213> ORGANISM: HOMO SAPIENS

<400> SEQUENCE: 66
ttcattagcc gtgtggatca                                                     20

<210> SEQ ID NO 67
<211> LENGTH: 20
<212> TYPE: DNA
<213> ORGANISM: HOMO SAPIENS

<400> SEQUENCE: 67
ttcattagcc gtgtggttca                                                     20

<210> SEQ ID NO 68
```

```
<211> LENGTH: 20
<212> TYPE: DNA
<213> ORGANISM: HOMO SAPIENS

<400> SEQUENCE: 68
ttcattagcc gtgtggctca                                               20

<210> SEQ ID NO 69
<211> LENGTH: 20
<212> TYPE: DNA
<213> ORGANISM: HOMO SAPIENS

<400> SEQUENCE: 69
ttctttagcc gtgtgggtca                                               20

<210> SEQ ID NO 70
<211> LENGTH: 20
<212> TYPE: DNA
<213> ORGANISM: HOMO SAPIENS

<400> SEQUENCE: 70
ttctttagcc gtgtggatca                                               20

<210> SEQ ID NO 71
<211> LENGTH: 20
<212> TYPE: DNA
<213> ORGANISM: HOMO SAPIENS

<400> SEQUENCE: 71
ttctttagcc gtgtggttca                                               20

<210> SEQ ID NO 72
<211> LENGTH: 20
<212> TYPE: DNA
<213> ORGANISM: HOMO SAPIENS

<400> SEQUENCE: 72
ttctttagcc gtgtggctca                                               20

<210> SEQ ID NO 73
<211> LENGTH: 20
<212> TYPE: DNA
<213> ORGANISM: HOMO SAPIENS

<400> SEQUENCE: 73
ttccttagcc gtgtgggtca                                               20

<210> SEQ ID NO 74
<211> LENGTH: 20
<212> TYPE: DNA
<213> ORGANISM: HOMO SAPIENS

<400> SEQUENCE: 74
ttccttagcc gtgtggatca                                               20

<210> SEQ ID NO 75
<211> LENGTH: 20
<212> TYPE: DNA
<213> ORGANISM: HOMO SAPIENS

<400> SEQUENCE: 75
ttccttagcc gtgtggttca                                               20

<210> SEQ ID NO 76
```

```
<211> LENGTH: 20
<212> TYPE: DNA
<213> ORGANISM: HOMO SAPIENS

<400> SEQUENCE: 76
ttccttagcc gtgtggctca                                              20

<210> SEQ ID NO 77
<211> LENGTH: 20
<212> TYPE: DNA
<213> ORGANISM: HOMO SAPIENS

<400> SEQUENCE: 77
ttggttagcc gtgtgggtca                                              20

<210> SEQ ID NO 78
<211> LENGTH: 20
<212> TYPE: DNA
<213> ORGANISM: HOMO SAPIENS

<400> SEQUENCE: 78
ttggttagcc gtgtggatca                                              20

<210> SEQ ID NO 79
<211> LENGTH: 20
<212> TYPE: DNA
<213> ORGANISM: HOMO SAPIENS

<400> SEQUENCE: 79
ttggttagcc gtgtggttca                                              20

<210> SEQ ID NO 80
<211> LENGTH: 20
<212> TYPE: DNA
<213> ORGANISM: HOMO SAPIENS

<400> SEQUENCE: 80
ttggttagcc gtgtggctca                                              20

<210> SEQ ID NO 81
<211> LENGTH: 20
<212> TYPE: DNA
<213> ORGANISM: HOMO SAPIENS

<400> SEQUENCE: 81
tttgttagcc gtgtgggtca                                              20

<210> SEQ ID NO 82
<211> LENGTH: 20
<212> TYPE: DNA
<213> ORGANISM: HOMO SAPIENS

<400> SEQUENCE: 82
tttgttagcc gtgtggatca                                              20

<210> SEQ ID NO 83
<211> LENGTH: 20
<212> TYPE: DNA
<213> ORGANISM: HOMO SAPIENS

<400> SEQUENCE: 83
tttgttagcc gtgtggttca                                              20

<210> SEQ ID NO 84
```

```
<211> LENGTH: 20
<212> TYPE: DNA
<213> ORGANISM: HOMO SAPIENS

<400> SEQUENCE: 84
tttgttagcc gtgtggctca                                               20

<210> SEQ ID NO 85
<211> LENGTH: 20
<212> TYPE: DNA
<213> ORGANISM: HOMO SAPIENS

<400> SEQUENCE: 85
ttgattagcc gtgtgggtca                                               20

<210> SEQ ID NO 86
<211> LENGTH: 20
<212> TYPE: DNA
<213> ORGANISM: HOMO SAPIENS

<400> SEQUENCE: 86
ttgattagcc gtgtggatca                                               20

<210> SEQ ID NO 87
<211> LENGTH: 20
<212> TYPE: DNA
<213> ORGANISM: HOMO SAPIENS

<400> SEQUENCE: 87
ttgattagcc gtgtggttca                                               20

<210> SEQ ID NO 88
<211> LENGTH: 20
<212> TYPE: DNA
<213> ORGANISM: HOMO SAPIENS

<400> SEQUENCE: 88
ttgattagcc gtgtggctca                                               20

<210> SEQ ID NO 89
<211> LENGTH: 20
<212> TYPE: DNA
<213> ORGANISM: HOMO SAPIENS

<400> SEQUENCE: 89
tttattagcc gtgtgggtca                                               20

<210> SEQ ID NO 90
<211> LENGTH: 20
<212> TYPE: DNA
<213> ORGANISM: HOMO SAPIENS

<400> SEQUENCE: 90
tttattagcc gtgtggatca                                               20

<210> SEQ ID NO 91
<211> LENGTH: 20
<212> TYPE: DNA
<213> ORGANISM: HOMO SAPIENS

<400> SEQUENCE: 91
tttattagcc gtgtggttca                                               20

<210> SEQ ID NO 92
```

```
<211> LENGTH: 20
<212> TYPE: DNA
<213> ORGANISM: HOMO SAPIENS

<400> SEQUENCE: 92
tttattagcc gtgtggctca                                              20

<210> SEQ ID NO 93
<211> LENGTH: 20
<212> TYPE: DNA
<213> ORGANISM: HOMO SAPIENS

<400> SEQUENCE: 93
ttgtttagcc gtgtgggtca                                              20

<210> SEQ ID NO 94
<211> LENGTH: 20
<212> TYPE: DNA
<213> ORGANISM: HOMO SAPIENS

<400> SEQUENCE: 94
ttgtttagcc gtgtggatca                                              20

<210> SEQ ID NO 95
<211> LENGTH: 20
<212> TYPE: DNA
<213> ORGANISM: HOMO SAPIENS

<400> SEQUENCE: 95
ttgtttagcc gtgtggttca                                              20

<210> SEQ ID NO 96
<211> LENGTH: 20
<212> TYPE: DNA
<213> ORGANISM: HOMO SAPIENS

<400> SEQUENCE: 96
ttgtttagcc gtgtggctca                                              20

<210> SEQ ID NO 97
<211> LENGTH: 20
<212> TYPE: DNA
<213> ORGANISM: HOMO SAPIENS

<400> SEQUENCE: 97 tttttagcc gtgtgggtca                                               20

<210> SEQ ID NO 98
<211> LENGTH: 20
<212> TYPE: DNA
<213> ORGANISM: HOMO SAPIENS

<400> SEQUENCE: 98 tttttagcc gtgtggatca                                               20

<210> SEQ ID NO 99
<211> LENGTH: 20
<212> TYPE: DNA
<213> ORGANISM: Homo sapiens

<400> SEQUENCE: 99 tttttagcc gtgtggttca                                               20

<210> SEQ ID NO 100
```

```
<211> LENGTH: 20
<212> TYPE: DNA
<213> ORGANISM: HOMO SAPIENS

<400> SEQUENCE: 100 tttttagcc gtgtggctca                                              20

<210> SEQ ID NO 101
<211> LENGTH: 20
<212> TYPE: DNA
<213> ORGANISM: HOMO SAPIENS

<400> SEQUENCE: 101
ttgcttagcc gtgtgggtca                                             20

<210> SEQ ID NO 102
<211> LENGTH: 20
<212> TYPE: DNA
<213> ORGANISM: HOMO SAPIENS

<400> SEQUENCE: 102
ttgcttagcc gtgtggttca                                             20

<210> SEQ ID NO 103
<211> LENGTH: 20
<212> TYPE: DNA
<213> ORGANISM: HOMO SAPIENS

<400> SEQUENCE: 103
ttgcttagcc gtgtggttca                                             20

<210> SEQ ID NO 104
<211> LENGTH: 20
<212> TYPE: DNA
<213> ORGANISM: HOMO SAPIENS

<400> SEQUENCE: 104
ttgcttagcc gtgtggctca                                             20

<210> SEQ ID NO 105
<211> LENGTH: 20
<212> TYPE: DNA
<213> ORGANISM: HOMO SAPIENS

<400> SEQUENCE: 105
tttcttagcc gtgtgggtca                                             20

<210> SEQ ID NO 106
<211> LENGTH: 20
<212> TYPE: DNA
<213> ORGANISM: HOMO SAPIENS

<400> SEQUENCE: 106
tttcttagcc gtgtggatca                                             20

<210> SEQ ID NO 107
<211> LENGTH: 20
<212> TYPE: DNA
<213> ORGANISM: HOMO SAPIENS

<400> SEQUENCE: 107
tttcttagcc gtgtggttca                                             20

<210> SEQ ID NO 108
```

```
<211> LENGTH: 20
<212> TYPE: DNA
<213> ORGANISM: HOMO SAPIENS

<400> SEQUENCE: 108
tttcttagcc gtgtggctca                                                  20

<210> SEQ ID NO 109
<211> LENGTH: 20
<212> TYPE: DNA
<213> ORGANISM: HOMO SAPIENS

<400> SEQUENCE: 109
ttagttagcc gtgtgggtca                                                  20

<210> SEQ ID NO 110
<211> LENGTH: 20
<212> TYPE: DNA
<213> ORGANISM: HOMO SAPIENS

<400> SEQUENCE: 110
ttagttagcc gtgtggatca                                                  20

<210> SEQ ID NO 111
<211> LENGTH: 20
<212> TYPE: DNA
<213> ORGANISM: HOMO SAPIENS

<400> SEQUENCE: 111
ttagttagcc gtgtggttca                                                  20

<210> SEQ ID NO 112
<211> LENGTH: 20
<212> TYPE: DNA
<213> ORGANISM: HOMO SAPIENS

<400> SEQUENCE: 112
ttagttagcc gtgtggctca                                                  20

<210> SEQ ID NO 113
<211> LENGTH: 20
<212> TYPE: DNA
<213> ORGANISM: HOMO SAPIENS

<400> SEQUENCE: 113
ttcgttagcc gtgtgggtca                                                  20

<210> SEQ ID NO 114
<211> LENGTH: 20
<212> TYPE: DNA
<213> ORGANISM: HOMO SAPIENS

<400> SEQUENCE: 114
ttcgttagcc gtgtggatca                                                  20

<210> SEQ ID NO 115
<211> LENGTH: 20
<212> TYPE: DNA
<213> ORGANISM: HOMO SAPIENS

<400> SEQUENCE: 115
ttcgttagcc gtgtggttca                                                  20

<210> SEQ ID NO 116
```

<211> LENGTH: 20
<212> TYPE: DNA
<213> ORGANISM: HOMO SAPIENS

<400> SEQUENCE: 116
ttcgttagcc gtgtggctca					20

<210> SEQ ID NO 117
<211> LENGTH: 20
<212> TYPE: DNA
<213> ORGANISM: HOMO SAPIENS

<400> SEQUENCE: 117
ttaattagcc gtgtgggtca					20

<210> SEQ ID NO 118
<211> LENGTH: 20
<212> TYPE: DNA
<213> ORGANISM: HOMO SAPIENS

<400> SEQUENCE: 118
ttaattagcc gtgtggatca					20

<210> SEQ ID NO 119
<211> LENGTH: 20
<212> TYPE: DNA
<213> ORGANISM: HOMO SAPIENS

<400> SEQUENCE: 119
ttaattagcc gtgtggttca					20

<210> SEQ ID NO 120
<211> LENGTH: 20
<212> TYPE: DNA
<213> ORGANISM: HOMO SAPIENS

<400> SEQUENCE: 120
ttaattagcc gtgtggctca					20

<210> SEQ ID NO 121
<211> LENGTH: 20
<212> TYPE: DNA
<213> ORGANISM: HOMO SAPIENS

<400> SEQUENCE: 121
ttcattagcc gtgtgggtca					20

<210> SEQ ID NO 122
<211> LENGTH: 20
<212> TYPE: DNA
<213> ORGANISM: HOMO SAPIENS

<400> SEQUENCE: 122
ttcattagcc gtgtggatca					20

<210> SEQ ID NO 123
<211> LENGTH: 20
<212> TYPE: DNA
<213> ORGANISM: HOMO SAPIENS

<400> SEQUENCE: 123
ttcattagcc gtgtggttca					20

<210> SEQ ID NO 124

```
<211> LENGTH: 20
<212> TYPE: DNA
<213> ORGANISM: HOMO SAPIENS

<400> SEQUENCE: 124
ttcattagcc gtgtggctca                                              20

<210> SEQ ID NO 125
<211> LENGTH: 20
<212> TYPE: DNA
<213> ORGANISM: HOMO SAPIENS

<400> SEQUENCE: 125
ttatttagcc gtgtgggtca                                              20

<210> SEQ ID NO 126
<211> LENGTH: 20
<212> TYPE: DNA
<213> ORGANISM: HOMO SAPIENS

<400> SEQUENCE: 126
ttatttagcc gtgtggatca                                              20

<210> SEQ ID NO 127
<211> LENGTH: 20
<212> TYPE: DNA
<213> ORGANISM: HOMO SAPIENS

<400> SEQUENCE: 127
ttatttagcc gtgtggttca                                              20

<210> SEQ ID NO 128
<211> LENGTH: 20
<212> TYPE: DNA
<213> ORGANISM: HOMO SAPIENS

<400> SEQUENCE: 128
ttatttagcc gtgtggctca                                              20

<210> SEQ ID NO 129
<211> LENGTH: 20
<212> TYPE: DNA
<213> ORGANISM: HOMO SAPIENS

<400> SEQUENCE: 129
ttctttagcc gtgtgggtca                                              20

<210> SEQ ID NO 130
<211> LENGTH: 20
<212> TYPE: DNA
<213> ORGANISM: HOMO SAPIENS

<400> SEQUENCE: 130
ttctttagcc gtgtggatca                                              20

<210> SEQ ID NO 131
<211> LENGTH: 20
<212> TYPE: DNA
<213> ORGANISM: HOMO SAPIENS

<400> SEQUENCE: 131
ttctttagcc gtgtggttca                                              20

<210> SEQ ID NO 132
```

-continued

```
<211> LENGTH: 20
<212> TYPE: DNA
<213> ORGANISM: HOMO SAPIENS

<400> SEQUENCE: 132
ttctttagcc gtgtggctca                                                 20

<210> SEQ ID NO 133
<211> LENGTH: 20
<212> TYPE: DNA
<213> ORGANISM: HOMO SAPIENS

<400> SEQUENCE: 133
ttacttagcc gtgtgggtca                                                 20

<210> SEQ ID NO 134
<211> LENGTH: 20
<212> TYPE: DNA
<213> ORGANISM: HOMO SAPIENS

<400> SEQUENCE: 134
ttacttagcc gtgtggatca                                                 20

<210> SEQ ID NO 135
<211> LENGTH: 20
<212> TYPE: DNA
<213> ORGANISM: HOMO SAPIENS

<400> SEQUENCE: 135
ttacttagcc gtgtggttca                                                 20

<210> SEQ ID NO 136
<211> LENGTH: 20
<212> TYPE: DNA
<213> ORGANISM: HOMO SAPIENS

<400> SEQUENCE: 136
ttacttagcc gtgtggctca                                                 20

<210> SEQ ID NO 137
<211> LENGTH: 20
<212> TYPE: DNA
<213> ORGANISM: HOMO SAPIENS

<400> SEQUENCE: 137
ttccttagcc gtgtgggtca                                                 20

<210> SEQ ID NO 138
<211> LENGTH: 20
<212> TYPE: DNA
<213> ORGANISM: HOMO SAPIENS

<400> SEQUENCE: 138
ttccttagcc gtgtggatca                                                 20

<210> SEQ ID NO 139
<211> LENGTH: 20
<212> TYPE: DNA
<213> ORGANISM: HOMO SAPIENS

<400> SEQUENCE: 139
ttccttagcc gtgtggttca                                                 20

<210> SEQ ID NO 140
```

```
<211> LENGTH: 20
<212> TYPE: DNA
<213> ORGANISM: HOMO SAPIENS

<400> SEQUENCE: 140
ttccttagcc gtgtggctca                                               20

<210> SEQ ID NO 141
<211> LENGTH: 16
<212> TYPE: DNA
<213> ORGANISM: HOO SAPIENS

<400> SEQUENCE: 141
gcttagccgt gtggca                                                   16

<210> SEQ ID NO 142
<211> LENGTH: 16
<212> TYPE: DNA
<213> ORGANISM: HOMO SAPIENS

<400> SEQUENCE: 142
acttagccgt gtggca                                                   16

<210> SEQ ID NO 143
<211> LENGTH: 16
<212> TYPE: DNA
<213> ORGANISM: HOMO SAPIENS

<400> SEQUENCE: 143
ccttagccgt gtggca                                                   16

<210> SEQ ID NO 144
<211> LENGTH: 16
<212> TYPE: DNA
<213> ORGANISM: HOMO SAPIENS

<400> SEQUENCE: 144
tggtagccgt gtggca                                                   16

<210> SEQ ID NO 145
<211> LENGTH: 16
<212> TYPE: DNA
<213> ORGANISM: HOMO SAPIENS

<400> SEQUENCE: 145
tgatagccgt gtggca                                                   16

<210> SEQ ID NO 146
<211> LENGTH: 16
<212> TYPE: DNA
<213> ORGANISM: HOMO SAPIENS

<400> SEQUENCE: 146
tgctagccgt gtggca                                                   16

<210> SEQ ID NO 147
<211> LENGTH: 16
<212> TYPE: DNA
<213> ORGANISM: HOMO SAPIENS

<400> SEQUENCE: 147
agttagccgt gtggca                                                   16

<210> SEQ ID NO 148
```

```
<211> LENGTH: 16
<212> TYPE: DNA
<213> ORGANISM: HOMO SAPIENS

<400> SEQUENCE: 148
cgttagccgt gtggca                                                    16

<210> SEQ ID NO 149
<211> LENGTH: 16
<212> TYPE: DNA
<213> ORGANISM: HOMO SAPIENS

<400> SEQUENCE: 149
aattagccgt gtggca                                                    16

<210> SEQ ID NO 150
<211> LENGTH: 16
<212> TYPE: DNA
<213> ORGANISM: HOMO SAPIENS

<400> SEQUENCE: 150
cattagccgt gtggca                                                    16

<210> SEQ ID NO 151
<211> LENGTH: 16
<212> TYPE: DNA
<213> ORGANISM: HOMO SAPIENS

<400> SEQUENCE: 151
gtttagccgt gtggca                                                    16

<210> SEQ ID NO 152
<211> LENGTH: 16
<212> TYPE: DNA
<213> ORGANISM: HOMO SAPIENS

<400> SEQUENCE: 152
atttagccgt gtggca                                                    16

<210> SEQ ID NO 153
<211> LENGTH: 16
<212> TYPE: DNA
<213> ORGANISM: HOMO SAPIENS

<400> SEQUENCE: 153
ctttagccgt gtggca                                                    16

<210> SEQ ID NO 154
<211> LENGTH: 16
<212> TYPE: DNA
<213> ORGANISM: HOMO SAPIENS

<400> SEQUENCE: 154
tgggagccgt gtggca                                                    16

<210> SEQ ID NO 155
<211> LENGTH: 16
<212> TYPE: DNA
<213> ORGANISM: HOMO SAPIENS

<400> SEQUENCE: 155
tgagagccgt gtggca                                                    16

<210> SEQ ID NO 156
```

```
<211> LENGTH: 16
<212> TYPE: DNA
<213> ORGANISM: HOMO SAPIENS

<400> SEQUENCE: 156
tgcgagccgt gtggca                                                        16

<210> SEQ ID NO 157
<211> LENGTH: 16
<212> TYPE: DNA
<213> ORGANISM: HOMO SAPIENS

<400> SEQUENCE: 157
tgtcagccgt gtggca                                                        16

<210> SEQ ID NO 158
<211> LENGTH: 16
<212> TYPE: DNA
<213> ORGANISM: HOMO SAPIENS

<400> SEQUENCE: 158
tggcagccgt gtggca                                                        16

<210> SEQ ID NO 159
<211> LENGTH: 16
<212> TYPE: DNA
<213> ORGANISM: HOMO SAPIENS

<400> SEQUENCE: 159
tgacagccgt gtggca                                                        16

<210> SEQ ID NO 160
<211> LENGTH: 16
<212> TYPE: DNA
<213> ORGANISM: HOMO SAPIENS

<400> SEQUENCE: 160
tgccagccgt gtggca                                                        16

<210> SEQ ID NO 161
<211> LENGTH: 16
<212> TYPE: DNA
<213> ORGANISM: HOMO SAPIENS

<400> SEQUENCE: 161
tgtaagccgt gtggca                                                        16

<210> SEQ ID NO 162
<211> LENGTH: 16
<212> TYPE: DNA
<213> ORGANISM: HOMO SAPIENS

<400> SEQUENCE: 162
tggaagccgt gtggca                                                        16

<210> SEQ ID NO 163
<211> LENGTH: 16
<212> TYPE: DNA
<213> ORGANISM: HOMO SAPIENS

<400> SEQUENCE: 163
tgaaagccgt gtggca                                                        16

<210> SEQ ID NO 164
```

```
<211> LENGTH: 16
<212> TYPE: DNA
<213> ORGANISM: HOMO SAPIENS

<400> SEQUENCE: 164
tgcaagccgt gtggca                                                    16

<210> SEQ ID NO 165
<211> LENGTH: 16
<212> TYPE: DNA
<213> ORGANISM: HOMO SAPIENS

<400> SEQUENCE: 165
tgttagccgt gtggca                                                    16

<210> SEQ ID NO 166
<211> LENGTH: 17
<212> TYPE: DNA
<213> ORGANISM: HOMO SAPIENS

<400> SEQUENCE: 166
tgttgggccg tgtggca                                                   17

<210> SEQ ID NO 167
<211> LENGTH: 17
<212> TYPE: DNA
<213> ORGANISM: HOMO SAPIENS

<400> SEQUENCE: 167
tgttaggccg tgtggca                                                   17

<210> SEQ ID NO 168
<211> LENGTH: 17
<212> TYPE: DNA
<213> ORGANISM: HOMO SAPIENS

<400> SEQUENCE: 168
tgttcggccg tgtggca                                                   17

<210> SEQ ID NO 169
<211> LENGTH: 17
<212> TYPE: DNA
<213> ORGANISM: HOMO SAPIENS

<400> SEQUENCE: 169
tgtttcgccg tgtggca                                                   17

<210> SEQ ID NO 170
<211> LENGTH: 17
<212> TYPE: DNA
<213> ORGANISM: HOMO SAPIENS

<400> SEQUENCE: 170
tgttgcgccg tgtggca                                                   17

<210> SEQ ID NO 171
<211> LENGTH: 17
<212> TYPE: DNA
<213> ORGANISM: HOMO SAPIENS

<400> SEQUENCE: 171
tgttacgccg tgtggca                                                   17

<210> SEQ ID NO 172
```

```
<211> LENGTH: 17
<212> TYPE: DNA
<213> ORGANISM: HOMO SAPIENS

<400> SEQUENCE: 172
tgttccgccg tgtggca                                                    17

<210> SEQ ID NO 173
<211> LENGTH: 17
<212> TYPE: DNA
<213> ORGANISM: HOMO SAPIENS

<400> SEQUENCE: 173
tgtttagccg tgtggca                                                    17

<210> SEQ ID NO 174
<211> LENGTH: 17
<212> TYPE: DNA
<213> ORGANISM: HOMO SAPIENS

<400> SEQUENCE: 174
tgttgagccg tgtggca                                                    17

<210> SEQ ID NO 175
<211> LENGTH: 17
<212> TYPE: DNA
<213> ORGANISM: HOMO SAPIENS

<400> SEQUENCE: 175
tgttaagccg tgtggca                                                    17

<210> SEQ ID NO 176
<211> LENGTH: 17
<212> TYPE: DNA
<213> ORGANISM: HOMO SAPIENS

<400> SEQUENCE: 176
tgttcagccg tgtggca                                                    17

<210> SEQ ID NO 177
<211> LENGTH: 17
<212> TYPE: DNA
<213> ORGANISM: HOMO SAPIENS

<400> SEQUENCE: 177
tgttttgccg tgtggca                                                    17

<210> SEQ ID NO 178
<211> LENGTH: 17
<212> TYPE: DNA
<213> ORGANISM: HOMO SAPIENS

<400> SEQUENCE: 178
tgttgtgccg tgtggca                                                    17

<210> SEQ ID NO 179
<211> LENGTH: 17
<212> TYPE: DNA
<213> ORGANISM: HOMO SAPIENS

<400> SEQUENCE: 179
tgttatgccg tgtggca                                                    17

<210> SEQ ID NO 180
```

```
<211> LENGTH: 17
<212> TYPE: DNA
<213> ORGANISM: HOMO SAPIENS

<400> SEQUENCE: 180
tgttctgccg tgtggca                                                 17

<210> SEQ ID NO 181
<211> LENGTH: 16
<212> TYPE: DNA
<213> ORGANISM: HOMO SAPIENS

<400> SEQUENCE: 181
gattagccgt gtggca                                                  16

<210> SEQ ID NO 182
<211> LENGTH: 16
<212> TYPE: DNA
<213> ORGANISM: HOMO SAPIENS

<400> SEQUENCE: 182
aattagccgt gtggca                                                  16

<210> SEQ ID NO 183
<211> LENGTH: 16
<212> TYPE: DNA
<213> ORGANISM: HOMO SAPIENS

<400> SEQUENCE: 183
cattagccgt gtggca                                                  16

<210> SEQ ID NO 184
<211> LENGTH: 16
<212> TYPE: DNA
<213> ORGANISM: HOMO SAPIENS

<400> SEQUENCE: 184
gtttagccgt gtggca                                                  16

<210> SEQ ID NO 185
<211> LENGTH: 16
<212> TYPE: DNA
<213> ORGANISM: HOMO SAPIENS

<400> SEQUENCE: 185
atttagccgt gtggca                                                  16

<210> SEQ ID NO 186
<211> LENGTH: 16
<212> TYPE: DNA
<213> ORGANISM: HOMO SAPIENS

<400> SEQUENCE: 186
ctttagccgt gtggca                                                  16

<210> SEQ ID NO 187
<211> LENGTH: 16
<212> TYPE: DNA
<213> ORGANISM: HOMO SAPIENS

<400> SEQUENCE: 187
tagtagccgt gtggca                                                  16

<210> SEQ ID NO 188
```

```
<211> LENGTH: 16
<212> TYPE: DNA
<213> ORGANISM: HOMO SAPIENS

<400> SEQUENCE: 188
tcgtagccgt gtggca                                              16

<210> SEQ ID NO 189
<211> LENGTH: 16
<212> TYPE: DNA
<213> ORGANISM: HOMO SAPIENS

<400> SEQUENCE: 189
ttgtagccgt gtggca                                              16

<210> SEQ ID NO 190
<211> LENGTH: 16
<212> TYPE: DNA
<213> ORGANISM: HOMO SAPIENS

<400> SEQUENCE: 190
tactagccgt gtggca                                              16

<210> SEQ ID NO 191
<211> LENGTH: 16
<212> TYPE: DNA
<213> ORGANISM: HOMO SAPIENS

<400> SEQUENCE: 191
tcctagccgt gtggca                                              16

<210> SEQ ID NO 192
<211> LENGTH: 16
<212> TYPE: DNA
<213> ORGANISM: HOMO SAPIENS

<400> SEQUENCE: 192
ttctagccgt gtggca                                              16

<210> SEQ ID NO 193
<211> LENGTH: 16
<212> TYPE: DNA
<213> ORGANISM: HOMO SAPIENS

<400> SEQUENCE: 193
taatagccgt gtggca                                              16

<210> SEQ ID NO 194
<211> LENGTH: 16
<212> TYPE: DNA
<213> ORGANISM: HOMO SAPIENS

<400> SEQUENCE: 194
tcatagccgt gtggca                                              16

<210> SEQ ID NO 195
<211> LENGTH: 16
<212> TYPE: DNA
<213> ORGANISM: HOMO SAPIENS

<400> SEQUENCE: 195
ttatagccgt gtggca                                              16

<210> SEQ ID NO 196
```

```
<211> LENGTH: 16
<212> TYPE: DNA
<213> ORGANISM: HOMO SAPIENS

<400> SEQUENCE: 196
taatagccgt gtggca                                               16

<210> SEQ ID NO 197
<211> LENGTH: 16
<212> TYPE: DNA
<213> ORGANISM: HOMO SAPIENS

<400> SEQUENCE: 197
tcctagccgt gtggca                                               16

<210> SEQ ID NO 198
<211> LENGTH: 16
<212> TYPE: DNA
<213> ORGANISM: HOMO SAPIENS

<400> SEQUENCE: 198
tgggagccgt gtggca                                               16

<210> SEQ ID NO 199
<211> LENGTH: 16
<212> TYPE: DNA
<213> ORGANISM: HOMO SAPIENS

<400> SEQUENCE: 199
taagagccgt gtggca                                               16

<210> SEQ ID NO 200
<211> LENGTH: 16
<212> TYPE: DNA
<213> ORGANISM: HOMO SAPIENS

<400> SEQUENCE: 200
tctgagccgt gtggca                                               16

<210> SEQ ID NO 201
<211> LENGTH: 16
<212> TYPE: DNA
<213> ORGANISM: HOMO SAPIENS

<400> SEQUENCE: 201
ttcgagccgt gtggca                                               16

<210> SEQ ID NO 202
<211> LENGTH: 16
<212> TYPE: DNA
<213> ORGANISM: HOMO SAPIENS

<400> SEQUENCE: 202
tggcagccgt gtggca                                               16

<210> SEQ ID NO 203
<211> LENGTH: 16
<212> TYPE: DNA
<213> ORGANISM: HOMO SAPIENS

<400> SEQUENCE: 203
taacagccgt gtggca                                               16

<210> SEQ ID NO 204
```

-continued

```
<211> LENGTH: 16
<212> TYPE: DNA
<213> ORGANISM: HOMO SAPIENS

<400> SEQUENCE: 204
tctcagccgt gtggca                                                          16

<210> SEQ ID NO 205
<211> LENGTH: 16
<212> TYPE: DNA
<213> ORGANISM: HOMO SAPIENS

<400> SEQUENCE: 205
ttccagccgt gtggca                                                          16

<210> SEQ ID NO 206
<211> LENGTH: 16
<212> TYPE: DNA
<213> ORGANISM: HOMO SAPIENS

<400> SEQUENCE: 206
tggaagccgt gtggca                                                          16

<210> SEQ ID NO 207
<211> LENGTH: 16
<212> TYPE: DNA
<213> ORGANISM: HOMO SAPIENS

<400> SEQUENCE: 207
taaaagccgt gtggca                                                          16

<210> SEQ ID NO 208
<211> LENGTH: 16
<212> TYPE: DNA
<213> ORGANISM: HOMO SAPIENS

<400> SEQUENCE: 208
tctaagccgt gtggca                                                          16

<210> SEQ ID NO 209
<211> LENGTH: 16
<212> TYPE: DNA
<213> ORGANISM: HOMO SAPIENS

<400> SEQUENCE: 209
ttcaagccgt gtggca                                                          16

<210> SEQ ID NO 210
<211> LENGTH: 16
<212> TYPE: DNA
<213> ORGANISM: HOMO SAPIENS

<400> SEQUENCE: 210
taatagccgt gtggca                                                          16

<210> SEQ ID NO 211
<211> LENGTH: 16
<212> TYPE: DNA
<213> ORGANISM: HOMO SAPIENS

<400> SEQUENCE: 211
tcctagccgt gtggca                                                          16

<210> SEQ ID NO 212
```

```
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 212
tnnnagccgt gtggca                                                       16

<210> SEQ ID NO 213
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 213
tnnnagccgt gtggca                                                       16

<210> SEQ ID NO 214
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 214
tnnnagccgt gtggca                                                       16

<210> SEQ ID NO 215
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 215
tnnnagccgt gtggca                                                       16

<210> SEQ ID NO 216
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 216
tnnnagccgt gtggca                                                       16

<210> SEQ ID NO 217
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 217
```

-continued tnnnagccgt gtggca 16

<210> SEQ ID NO 218
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 218
tnnnagccgt gtggca 16

<210> SEQ ID NO 219
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 219
tnnnagccgt gtggca 16

<210> SEQ ID NO 220
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 220
tnnnagccgt gtggca 16

<210> SEQ ID NO 221
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 221
tnnnagccgt gtggca 16

<210> SEQ ID NO 222
<211> LENGTH: 16
<212> TYPE: DNA
<213> ORGANISM: HOMO SAPIENS
<220> FEATURE:
<221> NAME/KEY: misc_feature
<222> LOCATION: (2)..(4)
<223> OTHER INFORMATION: n is a, c, g, or t

<400> SEQUENCE: 222
tnnnagccgt gtggca 16

<210> SEQ ID NO 223
<211> LENGTH: 16
<212> TYPE: DNA
<213> ORGANISM: HOMO SAPIENS
<220> FEATURE:
<221> NAME/KEY: misc_feature
<222> LOCATION: (2)..(4)

<223> OTHER INFORMATION: n is a, c, g, or t

<400> SEQUENCE: 223
tnnnagccgt gtggca                                                    16

<210> SEQ ID NO 224
<211> LENGTH: 16
<212> TYPE: DNA
<213> ORGANISM: HOMO SAPIENS

<400> SEQUENCE: 224
ggtgagccgt gtggca                                                    16

<210> SEQ ID NO 225
<211> LENGTH: 16
<212> TYPE: DNA
<213> ORGANISM: HOMO SAPIENS

<400> SEQUENCE: 225
agtgagccgt gtggca                                                    16

<210> SEQ ID NO 226
<211> LENGTH: 16
<212> TYPE: DNA
<213> ORGANISM: HOMO SAPIENS

<400> SEQUENCE: 226
cgtgagccgt gtggca                                                    16

<210> SEQ ID NO 227
<211> LENGTH: 16
<212> TYPE: DNA
<213> ORGANISM: HOMO SAPIENS

<400> SEQUENCE: 227
tgtgagccgt gtggca                                                    16

<210> SEQ ID NO 228
<211> LENGTH: 16
<212> TYPE: DNA
<213> ORGANISM: HOMO SAPIENS

<400> SEQUENCE: 228
ggtcagccgt gtggca                                                    16

<210> SEQ ID NO 229
<211> LENGTH: 16
<212> TYPE: DNA
<213> ORGANISM: HOMO SAPIENS

<400> SEQUENCE: 229
agtcagccgt gtggca                                                    16

<210> SEQ ID NO 230
<211> LENGTH: 16
<212> TYPE: DNA
<213> ORGANISM: HOMO SAPIENS

<400> SEQUENCE: 230
cgtcagccgt gtggca                                                    16

<210> SEQ ID NO 231
<211> LENGTH: 16
<212> TYPE: DNA

```
<213> ORGANISM: HOMO SAPIENS

<400> SEQUENCE: 231
gggaagccgt gtggca                                                    16

<210> SEQ ID NO 232
<211> LENGTH: 16
<212> TYPE: DNA
<213> ORGANISM: HOMO SAPIENS

<400> SEQUENCE: 232
agaaagccgt gtggca                                                    16

<210> SEQ ID NO 233
<211> LENGTH: 16
<212> TYPE: DNA
<213> ORGANISM: HOMO SAPIENS

<400> SEQUENCE: 233
cgcaagccgt gtggca                                                    16

<210> SEQ ID NO 234
<211> LENGTH: 16
<212> TYPE: DNA
<213> ORGANISM: HOMO SAPIENS

<400> SEQUENCE: 234
ggatagccgt gtggca                                                    16

<210> SEQ ID NO 235
<211> LENGTH: 16
<212> TYPE: DNA
<213> ORGANISM: HOMO SAPIENS

<400> SEQUENCE: 235
agctagccgt gtggca                                                    16

<210> SEQ ID NO 236
<211> LENGTH: 16
<212> TYPE: DNA
<213> ORGANISM: HOMO SAPIENS

<400> SEQUENCE: 236
ggttagccgg gtggca                                                    16

<210> SEQ ID NO 237
<211> LENGTH: 16
<212> TYPE: DNA
<213> ORGANISM: HOMO SAPIENS

<400> SEQUENCE: 237
agttagccgg gtggca                                                    16

<210> SEQ ID NO 238
<211> LENGTH: 16
<212> TYPE: DNA
<213> ORGANISM: HOMO SAPIENS

<400> SEQUENCE: 238
cgttagccgg gtggca                                                    16

<210> SEQ ID NO 239
<211> LENGTH: 16
<212> TYPE: DNA
```

<213> ORGANISM: HOMO SAPIENS

<400> SEQUENCE: 239
tgttagccgg gtggca                                                      16

<210> SEQ ID NO 240
<211> LENGTH: 16
<212> TYPE: DNA
<213> ORGANISM: HOMO SAPIENS

<400> SEQUENCE: 240
ggttagccgc gtggca                                                      16

<210> SEQ ID NO 241
<211> LENGTH: 16
<212> TYPE: DNA
<213> ORGANISM: HOMO SAPIENS

<400> SEQUENCE: 241
agttagccgc gtggca                                                      16

<210> SEQ ID NO 242
<211> LENGTH: 16
<212> TYPE: DNA
<213> ORGANISM: HOMO SAPIENS

<400> SEQUENCE: 242
cgttagccgc gtggca                                                      16

<210> SEQ ID NO 243
<211> LENGTH: 16
<212> TYPE: DNA
<213> ORGANISM: HOMO SAPIENS

<400> SEQUENCE: 243
tgttagccgc gtggca                                                      16

<210> SEQ ID NO 244
<211> LENGTH: 16
<212> TYPE: DNA
<213> ORGANISM: HOMO SAPIENS

<400> SEQUENCE: 244
gggtagccga gtggca                                                      16

<210> SEQ ID NO 245
<211> LENGTH: 16
<212> TYPE: DNA
<213> ORGANISM: HOMO SAPIENS

<400> SEQUENCE: 245
agatagccga gtggca                                                      16

<210> SEQ ID NO 246
<211> LENGTH: 16
<212> TYPE: DNA
<213> ORGANISM: HOMO SAPIENS

<400> SEQUENCE: 246
cgctagccga gtggca                                                      16

<210> SEQ ID NO 247
<211> LENGTH: 16
<212> TYPE: DNA

-continued

<213> ORGANISM: HOMO SAPIENS

<400> SEQUENCE: 247
tgttagccga gtggca                                                16

<210> SEQ ID NO 248
<211> LENGTH: 16
<212> TYPE: DNA
<213> ORGANISM: HOMO SAPIENS

<400> SEQUENCE: 248
ggttagccgg ggggca                                                16

<210> SEQ ID NO 249
<211> LENGTH: 16
<212> TYPE: DNA
<213> ORGANISM: HOMO SAPIENS

<400> SEQUENCE: 249
agttagccgg ggggca                                                16

<210> SEQ ID NO 250
<211> LENGTH: 16
<212> TYPE: DNA
<213> ORGANISM: HOMO SAPIENS

<400> SEQUENCE: 250
cgttagccgg ggggca                                                16

<210> SEQ ID NO 251
<211> LENGTH: 16
<212> TYPE: DNA
<213> ORGANISM: HOMO SAPIENS

<400> SEQUENCE: 251
tgttagccgg ggggca                                                16

<210> SEQ ID NO 252
<211> LENGTH: 16
<212> TYPE: DNA
<213> ORGANISM: HOMO SAPIENS

<400> SEQUENCE: 252
ggttagccgc gcggca                                                16

<210> SEQ ID NO 253
<211> LENGTH: 16
<212> TYPE: DNA
<213> ORGANISM: HOMO SAPIENS

<400> SEQUENCE: 253
agttagccgc gcggca                                                16

<210> SEQ ID NO 254
<211> LENGTH: 16
<212> TYPE: DNA
<213> ORGANISM: HOMO SAPIENS

<400> SEQUENCE: 254
cgttagccgc gcggca                                                16

<210> SEQ ID NO 255
<211> LENGTH: 16
<212> TYPE: DNA

```
<213> ORGANISM: HOMO SAPIENS

<400> SEQUENCE: 255
tgttagccgc gcggca                                               16

<210> SEQ ID NO 256
<211> LENGTH: 16
<212> TYPE: DNA
<213> ORGANISM: HOMO SAPIENS

<400> SEQUENCE: 256
gggtagccga gaggca                                               16

<210> SEQ ID NO 257
<211> LENGTH: 16
<212> TYPE: DNA
<213> ORGANISM: HOMO SAPIENS

<400> SEQUENCE: 257
agatagccga gaggca                                               16

<210> SEQ ID NO 258
<211> LENGTH: 16
<212> TYPE: DNA
<213> ORGANISM: HOMO SAPIENS

<400> SEQUENCE: 258
cgctagccga gaggca                                               16

<210> SEQ ID NO 259
<211> LENGTH: 16
<212> TYPE: DNA
<213> ORGANISM: HOMO SAPIENS

<400> SEQUENCE: 259
tgttagccga gaggca                                               16
```

OLIGOMER SEQUENCES MAPPING

CROSS-REFERENCE TO RELATED APPLICATIONS

This application claims priority to provisional application Ser. No. 61/149,689, filed Feb. 3, 2009, which is hereby incorporated by reference in its entirety.

BACKGROUND OF THE INVENTION

Genetic studies have seen rapid advances in recent years. The entire genomes of specific organisms, including some individual human beings, have been sequenced and become available as references. In genetic research, genetic testing, personalized medicine, and many other applications, it is often useful to obtain a sample of genetic material, determine a sequence of that sample, and to map that sample sequence to a location on an available reference. Once the mapping is done, a comparison can be made to a reference in order to identify polymorphisms or mutations or obtain other useful information.

Existing approaches typically map long, contiguous sample sequences to locations in a reference. However, some techniques used for obtaining sample sequences yield data sets comprising short sequences (sometimes referred to as oligomers) with predicted spatial relationships. Such 'polyoligomer data sets' consist of multiple oligomers that have variable but constrained amounts of spacing or overlap (referred to as separation distance) between oligomers. Where individual oligomers are too short to identify one or a small number of possible locations on a reference, and the spacing between oligomers is variable, existing approaches are not adequate.

It would be useful to have a way of accurately mapping relatively short oligomer sequences with variable separation distances to a reference in a manner that would both be robust to and identify data errors, mutations, or polymorphisms. It would also be desirable for such mapping to be efficient both in terms of computational speed and cost.

SUMMARY OF THE INVENTION

The present invention provides methods of analyzing polyoligomer data sets by comparing keys generated from the data sets to an index of keys generated from the reference. Keys created from a polyoligomer data set can be compared to the reference index to map the polyoligomer data set to candidate locations on the reference.

In one implementation, the invention provides a method of oligomer sequence mapping, comprising receiving a data set of related oligomer sequences, applying one or more key patterns to the oligomer sequences in the data set to generate one or more initial keys, modifying one or more positions within the initial key to create a set of modified keys, and comparing the modified keys to a reference index to determine candidate locations of the oligomer sequences in the reference.

In another implementation, the invention provides a method of oligomer sequence mapping, comprising receiving a data set of related oligomer sequences, modifying one or more positions within the data set, applying one or more key patterns to the oligomer sequences in the data set to generate one or more modified keys, and comparing the modified keys to a reference index to determine candidate locations of the oligomer sequences in the reference.

In specific implementations, the positions modified by substituting other bases in the modified positions, while keeping the initial bases of the remaining positions of the key and/or data set. The positions may be substituted individually or as sets of two or more positions ("combined positions"), with all remaining positions of the key and/or data set remaining constant. The substitutions can involve arbitrary combinations of positions (including enumeration of all possible combinations of some fixed number of positions), combinations of positions based on specific spatial arrangements (e.g. adjacent positions), combinations positions based on other criteria, e.g., low data quality scores at specific positions, or combinations of more than one of the above. Preferably, the substitutions reflect all possible bases that could be present at the substituted positions.

In specific implementations, at every step a subset of positions is selected for substitution. The subsets are organized so that all or a majority of the bases fall in one or more of these subsets. Thus, over the combination of all substitution steps, all or a majority of the individual bases in a key will be separately substituted, to create the set of substituted keys. In a more specific implementation, every subset consists of a single base, so that all of the bases in a key are individually substituted.

For each position, a set of substituted keys is created, replacing the base at the substituted position with each of the alternative nucleic acids. The set of substituted keys is searched in the reference index to identify candidate locations. The substitutions can be made in the data set before key generation, or following key generation and/or reordering but prior to searching for the keys in the index.

In other specific implementations, the bases in a key and/or a data set are substituted in pairs, or multiple bases (referred to as "combined bases"). Although in specific implementations described herein the pairs or multiple bases are illustrated as being adjacent, the present invention is intended to cover any selection of two or more bases at a time for substitution, without restriction to how such bases were selected. Thus, the substitutions can be made sequentially, using adjacent or overlapping pairs, triplets, or multiple base units, or without regard to position in the key, e.g., combined bases selected by other criteria, e.g., low data quality scores. In specific implementations, the substitutions can be arbitrary sets of 1, 2 or 3 bases selected by application of selected criteria. The substitutions can be made in the data set before key generation, or following key generation and/or reordering but prior to mapping of the keys to the index. These substitutions in the key are thus made as all possible base combinations of the combined bases, and the substituted keys used to search the reference index.

In other specific implementations, modified keys may be created based on inserting or deleting one or more bases at positions within the initial key, while retaining the positions of the other bases in the initial key.

In certain implementations, multiple modification regimes can be used together to identify candidate location in a reference and/or validate locations within the reference. For example, single base substitutions at each position within a key can be used in conjunction with substitution of low scoring bases to aid in confirming candidate locations having a difference in the data set sequence as compared to the reference. In another example, two different combined base modification regimes can be used together (e.g., insertion or deletion of single bases at each position within a key together with sequential substitution of alternative bases at low scoring positions).

In addition to the combined regimes above, other specific combined regimes may be useful in circumstances such as confirmation of the addition or deletion of a position in the data set as compared to the reference in the presence of additional sequencing errors. They are also useful to confirm a mutation or polymorphism in the data set that differs from the sequence of the reference. Thus, combinations of base substitution regimes can be especially useful to identify or confirm novel sequences in the data set that differ from a reference.

In some implementations, the positions of the data set may be reordered prior to mapping, e.g., to generate a key based on statistical likelihood of the presence of specific positions in a data set. In certain implementations, the data set is reordered prior to application of a key pattern. In another implementation, the key is reordered following application of the key pattern to the data set.

In another implementation of the invention, an oligomer sequence mapping system is provided, comprising: an interface configured to receive a data set of related oligomer sequences and a processor coupled to the interface. This processor is configured to apply one or more key patterns to information in the data set to generate one or more keys from the data set, to sequentially substitute, insert or delete the majority or all of the positions within the key to create a set of substituted keys that reflect all possibilities of bases at the modified positions, and to compare the keys generated from the data set and the substituted keys to a reference index to determine candidate locations of the oligomer sequences in the reference. In certain aspects, this system is further configured to output locations of the oligomer sequences in the reference. The positions may be substituted as single bases or combined bases. The system is also configured to perform multiple modification regimes within a single data set and/or key, as described above.

In another implementation, a computer program product for oligomer sequence mapping is provided. This computer program product is in a computer readable medium, and provides instructions for receiving a data set of related oligomer sequences; applying one or more key patterns to information in the data set to generate one or more keys; modifying one or more of the positions of a key; and comparing the modified keys to a reference index to determine candidate locations of the oligomer sequences in the reference. The positions within the key may be substituted as single positions, or as pairs, triplets, or multiple base combinations, and preferably reflect all possible bases at the substituted positions. The system can also be configured to validate candidate locations.

In another implementation, a computer program product for oligomer sequence mapping is provided. This computer program product is in a computer readable medium, and provides instructions for receiving a data set of related oligomer sequences; applying one or more key patterns to information in the data set to generate one or more initial keys; substituting the majority or all of the positions of a key; modifying one or more positions reflect all possible combinations of substitutions or insertion or deletion of bases at these positions; and comparing the substituted keys to a reference index to determine candidate locations of the oligomer sequences in the reference. The positions within the key may be substituted as one or more bases, and preferably reflect all possible bases at the substituted positions. The product also provides instructions to validate candidate locations.

BRIEF DESCRIPTION OF THE DRAWINGS

Various implementations of the invention are disclosed in the following detailed description and the accompanying drawings. These are for exemplary purposes only, and not intended to limit the scope of the invention, which shall only be limited by the claims.

FIG. 4A is a schematic illustration of an index.

DETAILED DESCRIPTION

Figure 1A:
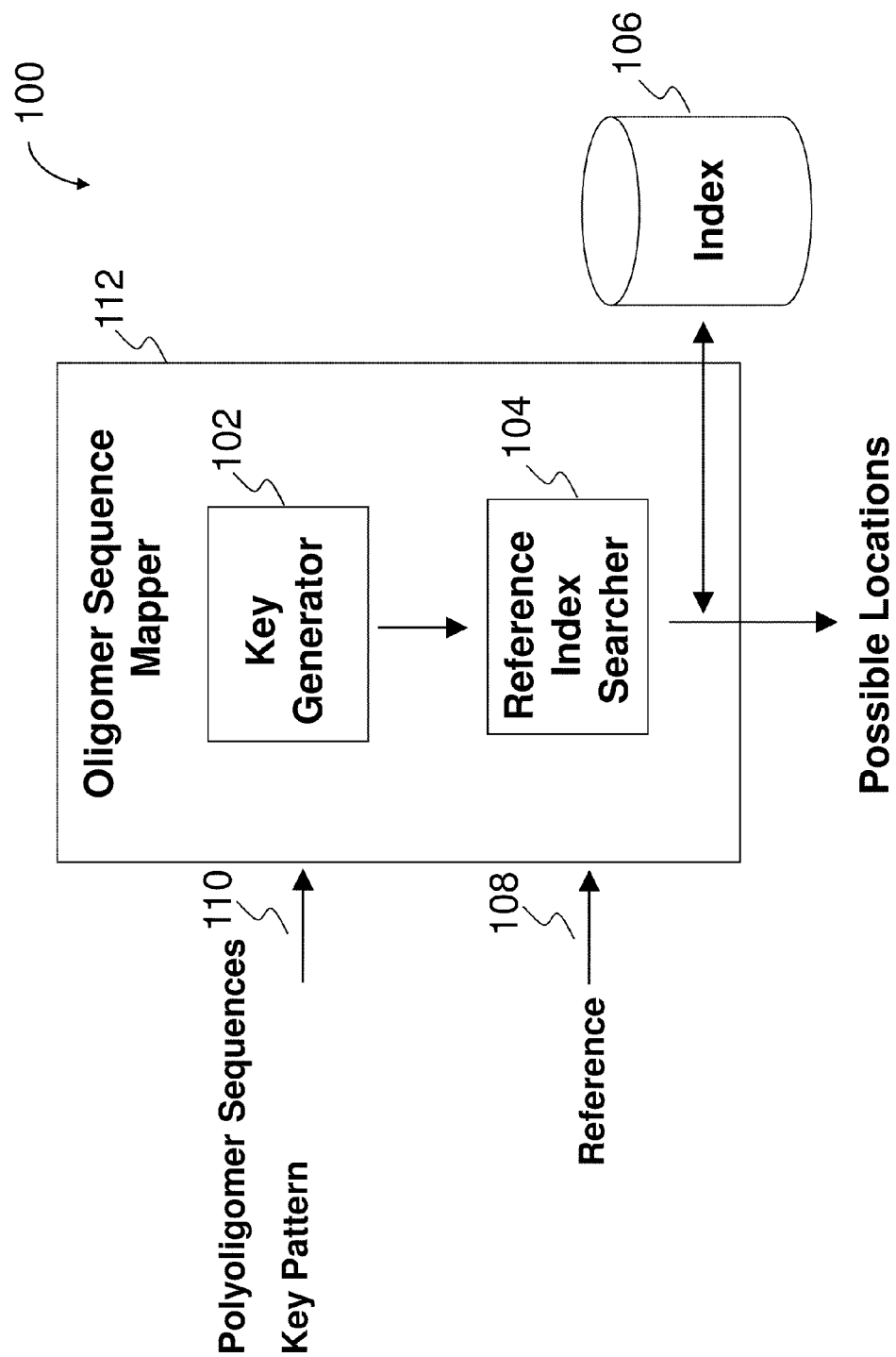
FIG. 1A is a block diagram illustrating an implementation of a system for mapping oligomer sequences.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any implementation. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

DEFINITIONS

The term "polyoligomer data set" (also, simply "polyoligomer" or "data set") refers to a collection of two or more determined oligomer sequences (e.g. using a biochemical process), and whose separations from one another are, or for computational purposes are assumed to be, restricted to certain known or estimated values.

The term "reference" refers to a known sequence of nucleotides. It may be an entire genome sequence of a reference organism, a portion of a reference genome, a consensus sequence of many reference organisms, a compilation sequence based on different components of different organisms, or any other appropriate sequence. It may also include information regarding variations of the reference known to be found in a population of organisms.

The term "reference index" refers to an index relating keys consisting of sequences of bases to locations in the reference that is created by application of one or more key patterns to a reference.

The term "sequence relationship" refers to a known, inferred or hypothesized specification of separation distances among two or more oligomers, e.g. defined as the number of (unknown) bases between two oligomers. The sequence relationship may be a separation distance, an overlap distance, or the two oligos may be directly adjacent to one another in the reference.

The term "instantiation" refers to the derivation of a sequence of contiguous bases, some known, some possibly unknown, by applying a specific set of sequence relationships to a polyoligomer data set. The term may also refer to the derived sequence itself, which may otherwise be called an "instantiated polyoligomer".

The term "mapping" refers to a process which relates a polyoligomer to zero, one or more locations in the reference to which the polyoligomer is similar, e.g., by matching the instantiated polyoligomer to one or more keys within an index of the invention corresponding to a location within a reference.

The term "candidate locations" refers to potential locations in a reference of oligomers of a data set identified based on the generation of keys from the data set and the mapping of these keys using a reference index. Since a key derived from a given polyoligomer does not necessarily include all bases of the polyoligomer, the polyoligomer may or may not be a perfect match with a given candidate location in a reference.

The phrase "perfect match" means an exact data match between one possible instantiation and the reference. In certain implementations, an unknown base in a data set may be considered to be a perfect match to any base.

The term "validated locations" means candidate locations which have been further confirmed to be locations within a reference that are compatible with a polyoligomer.

The phrase "degree of conservation" as used herein refers to the likelihood that one or more of the bases in the oligomer sequences of a data set will be in a given position in the key when the key pattern is applied to the correct instantiation of the data set.

The term "sample analysis" means any use of the information obtained through use of the keys and indexes of the invention, including but not limited to genomic analysis (including sequence assembly), polymorphism analysis, mutation analysis, phylogenetic analysis and the like.

The term "key pattern" refers to a predetermined spatial relationship that is used to derive one or more keys from a reference and/or an instantiated polyoligomer.

The Invention in General

Mapping of polyoligomer data sets to locations in a reference is disclosed. The oligomer sequences are obtained from a sample of genetic material (such as DNA or RNA molecules from an organism), e.g., by subjecting the sample or a fragment thereof to a biochemical process. The oligomer sequences are mapped to one or more possible locations in a reference and those locations are output to facilitate further sample analysis.

In some embodiments, an index is generated for mapping key sequences to locations in the reference. The key sequences in the index are generated based on the reference and key patterns that are derived from expected oligomer sequence relationships. Examples of such oligomer sequence relationships include oligomer sequence length, the likely amount of spacing or overlap between oligomer sequences (also referred to as "separation distance"), the statistical distribution of these separation distances (the "distance variations"), and the statistical distribution of possible combinations of distance variations for sets of related oligomer sequences. The relationships may be determined based on existing knowledge about the biochemical process used to generate the oligomer sequences (i.e., based on oligomer sequences that would be expected to be obtained if the biochemical process were applied to a sample), empirical estimates based on preliminary analysis of oligomer sequences, estimation by experts, or other appropriate techniques.

The oligomer sequence relationships depend at least in part on the biochemical process used to generate the oligomers. Numerous processes can be used to generate oligomer data sets for use with the present invention. These include, but are not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; 7,329,496 and Margulies, et al. (2005), *Nature* 437:376-380 and Ronaghi, et al. (1996), *Anal. Biochem.* 242:84-89; ligation-based methods as disclosed in U.S. Pat. No. 6,306,597, WO2006073504, WO2007120208, all of which are incorporated by reference in their entirety. In a specific implementation, a Combinatorial Probe Anchor Ligation (cPAL) process is used in some embodiments (see U.S. Ser. No. 11/679,124, filed Feb. 24, 2007, which is incorporated herein by reference in its entirety).

The processes used to generate related oligomers in data sets may result in oligomers of various sizes, including different sizes within single data sets. For purposes of example only, and not to be limiting in scope, the oligomer sequences discussed in detail below for purposes of illustration are described as having a length of 6 bases, and a distance variation of +/−2 or +/−3 bases. It will be apparent to one skilled in the art upon reading the present disclosure that other sequence lengths and distance variations (e.g., +/−1 or +/−4) can be used in the described implementations.

The key generator also receives as one of its inputs one or more key patterns. The key patterns are derived from one or more oligomer sequence relationships. In some embodiments, various key patterns for different oligomer relationships are derived prior to the mapping process, stored, and retrieved as needed.

FIG. 1A is a block diagram illustrating an implementation of a system for mapping oligomer sequences onto a reference. In this example, the system 100 includes a communication interface 110 configured to receive inputs. Examples of a communication interface include without limitation external connections, such as a port, cable, wire line or wireless network interface card, etc., and internal connections such as a communication bus. The interface 110 is coupled to an oligomer sequence mapper component 112, which includes a key generator 102 and a reference index search engine 104. The key generator receives as one of its inputs a set of related oligomer sequences, e.g., a polyoligomer data set, and receives as another of its inputs one or more key patterns. When mapped to the reference, the related oligomer sequences are expected to be located with respect to each other within a small range of expected separation distance. The oligomer sequence relationships may include the separation distance or other relationships or expected correlations between oligomers.

Based on its inputs, the key generator generates one or more keys, which are strings of base sequences, compressed representations of base sequences or any other appropriate representations of base sequences that are suitable for computer processing. Using the keys, a reference index search engine 104 queries an index 106 to determine possible locations of the oligomer sequences in a reference 108. In the examples discussed below, keys within index 106 include strings that are permutations of bases. The index maps keys to their respective possible locations in the reference. These candidate locations are then examined to confirm the match between a data set and a given location, by comparison to the reference 108. The validated locations may be output and used for further sample analysis, which can have applications in genetic research, genetic testing, personalized medicine including diagnosis, prognosis and identification of predispositions, and the like.

An oligomer sequence mapper 112 with key generator 102, reference search engine 104, and index 106 are shown as separate logical components in the diagram. In some embodiments the components are separate components such as separate processors or separate processes operating on one processor, and in some embodiments some of the components may be combined and implemented on the same device, as a single integrated circuit, and/or as parts in the same process operating on a processor.

Figure 1B:
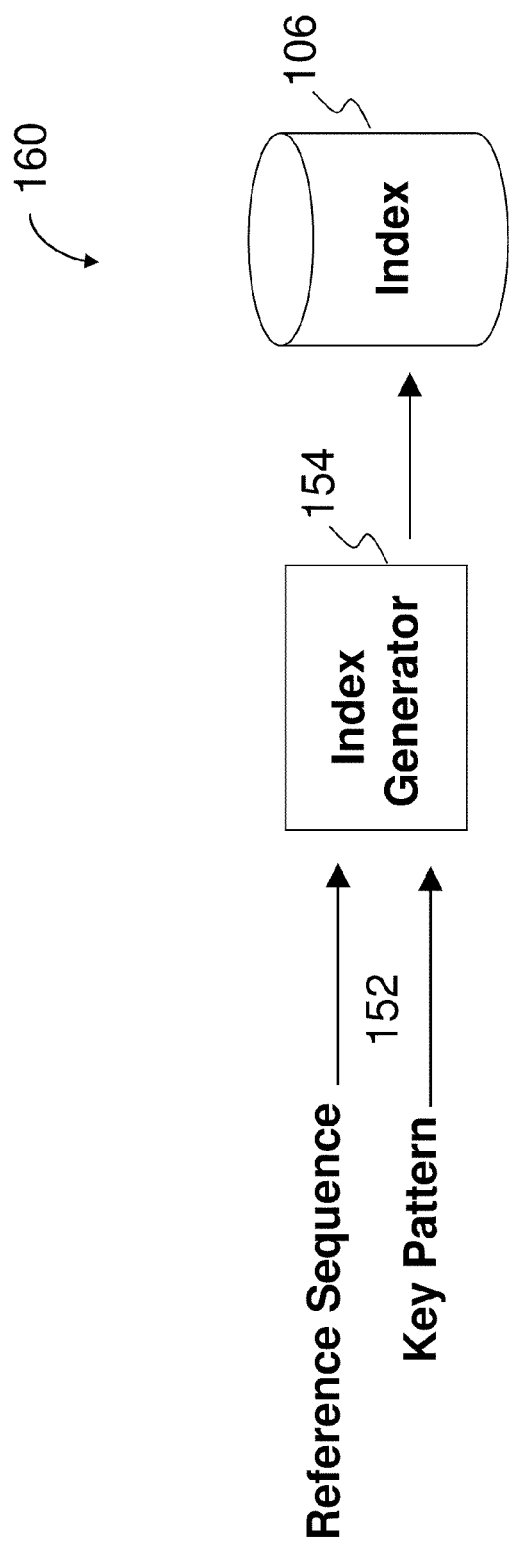
FIG. 1B is a block diagram illustrating an implementation of a system for generating an index.

FIG. 1B is a block diagram illustrating an implementation of a system for generating an index. System 160 may also include a general purpose computer and/or specialized hardware. In this example, system 160 includes an interface 152, which is configured to receive inputs such as the reference and one or more key patterns. The interface is coupled to an index generator 154 that includes a processor configured to generate keys based on the inputs. Keys and the locations from which they are derived are maintained in index 106, which may be stored on a computer readable storage medium such as a computer data storage device (e.g., random access memory), disk storage, and/or any other appropriate storage device. Such storage devices are optionally coupled with a central processing unit.

The keys for a specific data set are generated by applying pre-defined key patterns to the data set, and the obtained keys can then be compared to keys within a reference index. In certain implementations, the key patterns are applied directly to the data set without any further manipulation of the initial data obtained. In other implementations, the sequences of the data set may be further manipulated, e.g., re-ordered, or homopolymer-compressed; the key pattern is then applied to such derived sequences, and the resulting keys are compared to a reference index whose keys have been similarly manipulated In specific aspects, the keys obtained by applying the key pattern to a data set or a portion of a data set can be reverse-complemented. Preferably, the data set may be reverse complemented and the key pattern applied to obtain the keys. In other instances, the data set may be reverse complemented after the key pattern is applied but before comparison of the keys to a reference index This technique, in which the both the obtained keys and the complement keys (based on the key pattern) are searched within a reference index allows simultaneous searching for candidate locations in both strands of a sequence in a double-stranded molecule, e.g., DNA. Using such a technique effectively allows interrogation of both the forward strand sequence and the reverse strand sequence in a single process step using an index that is roughly half the size of an index containing all possible keys for both strand sequences.

In other specific aspects, the degree of conservation of specific positions within a key pattern can be used to re-order the key to prioritize positions with the highest degree of conservation (and thus likelihood that the position will be included in the key pattern). This is especially useful if there are potentially gaps in the data of the polyoligomer data sets, as the missing data will not then prevent analysis of the available data.

In some implementations, the use of multiple indexes is employed. When the relationships amongst the oligomers of a data set are sufficiently constrained, a single index will often suffice. If relationships amongst the oligomers of a data set are more variable, however, it may be advantageous to use multiple indexes instead of a single index. One example of this would include the use of multiple indexes where each is created using a single key pattern. This enables, for instance, a large range of separation distances while retaining key length/specificity, as discussed further below. Another example is to use multiple subsets of a reference based on key characteristics, e.g., separate indexes for keys beginning with each of the possible nucleotides.

Index Generation

Figure 2:
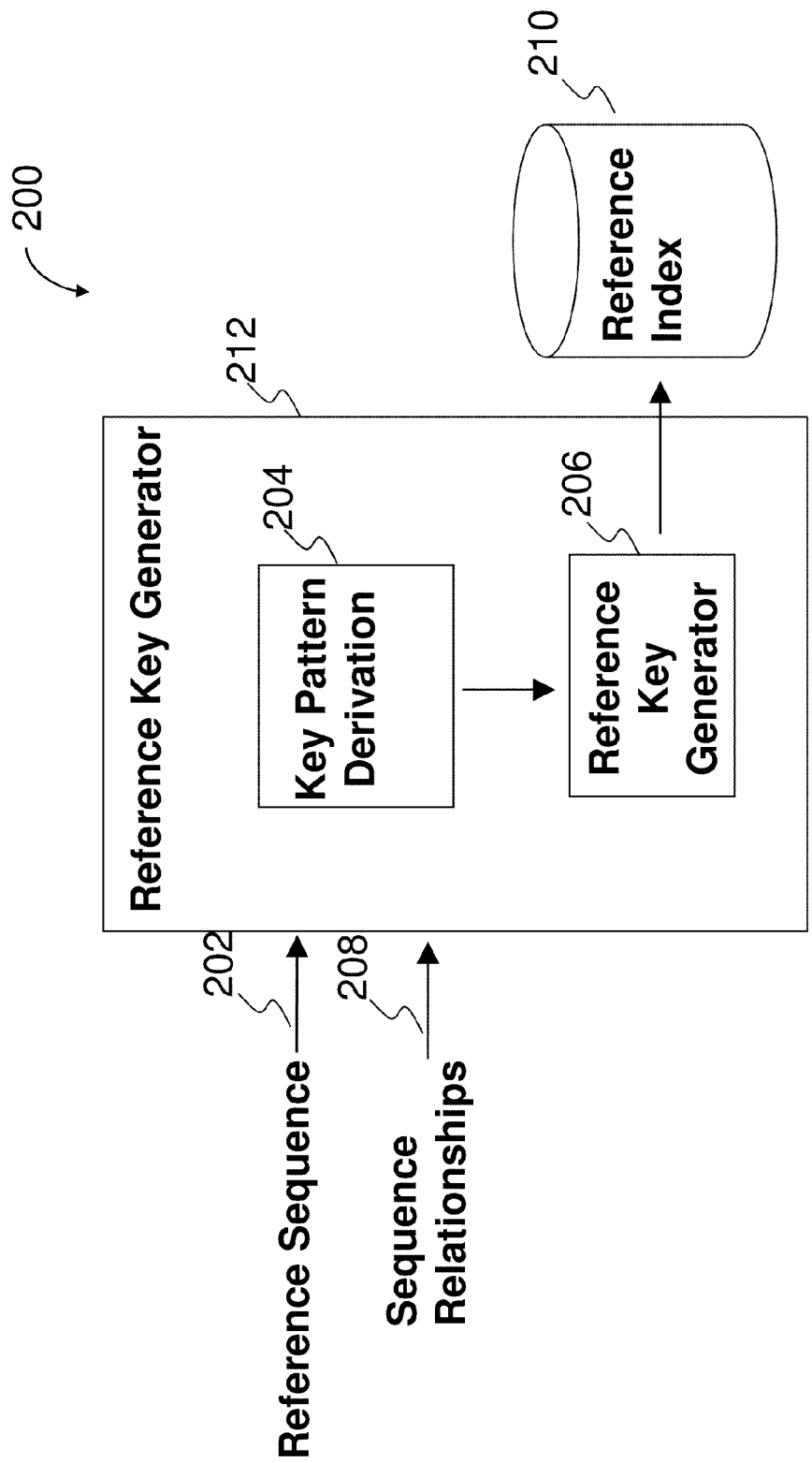
FIG. 2 is a flowchart illustrating an implementation of a process for generating the index.

FIG. 2 is a flowchart illustrating an embodiment of a process for generating the index. Process 200 may be implemented using an index generator such as 154 of FIG. 1B. A reference 202 and potential data set sequence relationships 208 are received by the reference key generator 212. At 204, one or more key patterns are derived, as described further below. At 206, the derived key patterns are applied to the reference to obtain keys in the index for mapping sequence strings to possible locations in the reference. In some embodiments, multiple indexes are generated from multiple key patterns.

Figure 3A:
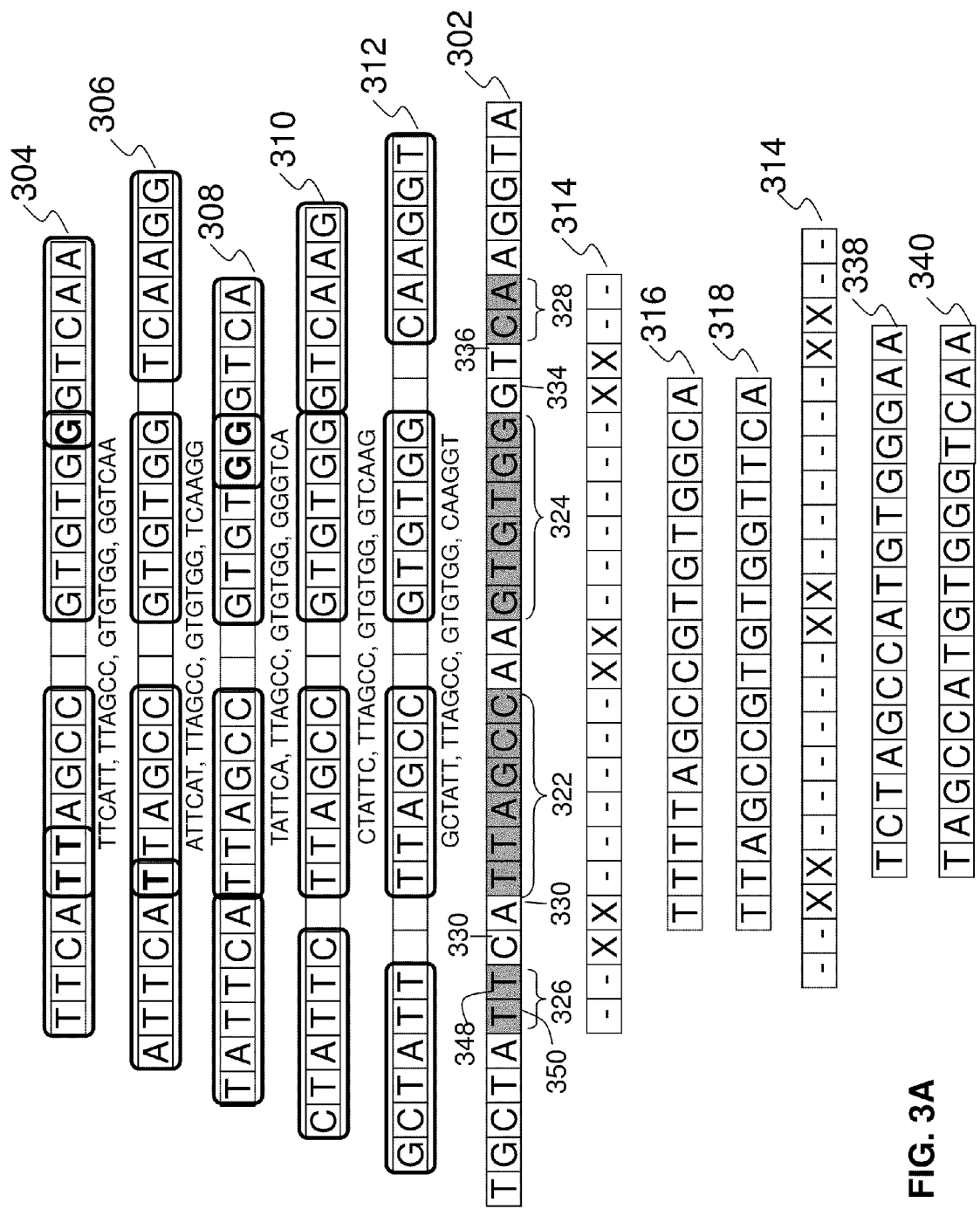
FIGS. 3A-3C are diagrams illustrating examples of key patterns derived from different sets of oligomer sequence relationships.

In some embodiments, once a key pattern is obtained, keys can be generated by repeatedly comparing the key pattern to the reference, each time sliding the key pattern forward by 1 base to a new location on the reference. The key-location mapping data is stored in an index. FIG. 3A exemplifies key generation for use in an index. Assuming that key pattern 314 is initially applied to reference 302 starting at location 350*a* key 316 is produced for this location. This key can reflect the direct order of sequence within the reference 316, or the bases obtained from the application of the key pattern to the reference may be reordered 318 based on confidence levels to improve mapping performance as described in more detail herein. Advancing along sequence 302 by one base, the key pattern 314 is applied again starting at the next location 348. A new key is produced for the new location, again having either a direct sequence 338 or a re-ordered sequence 340. By repeating the process for the entire length of the reference, each potential location within the reference is mapped to a key.

Figure 3B:
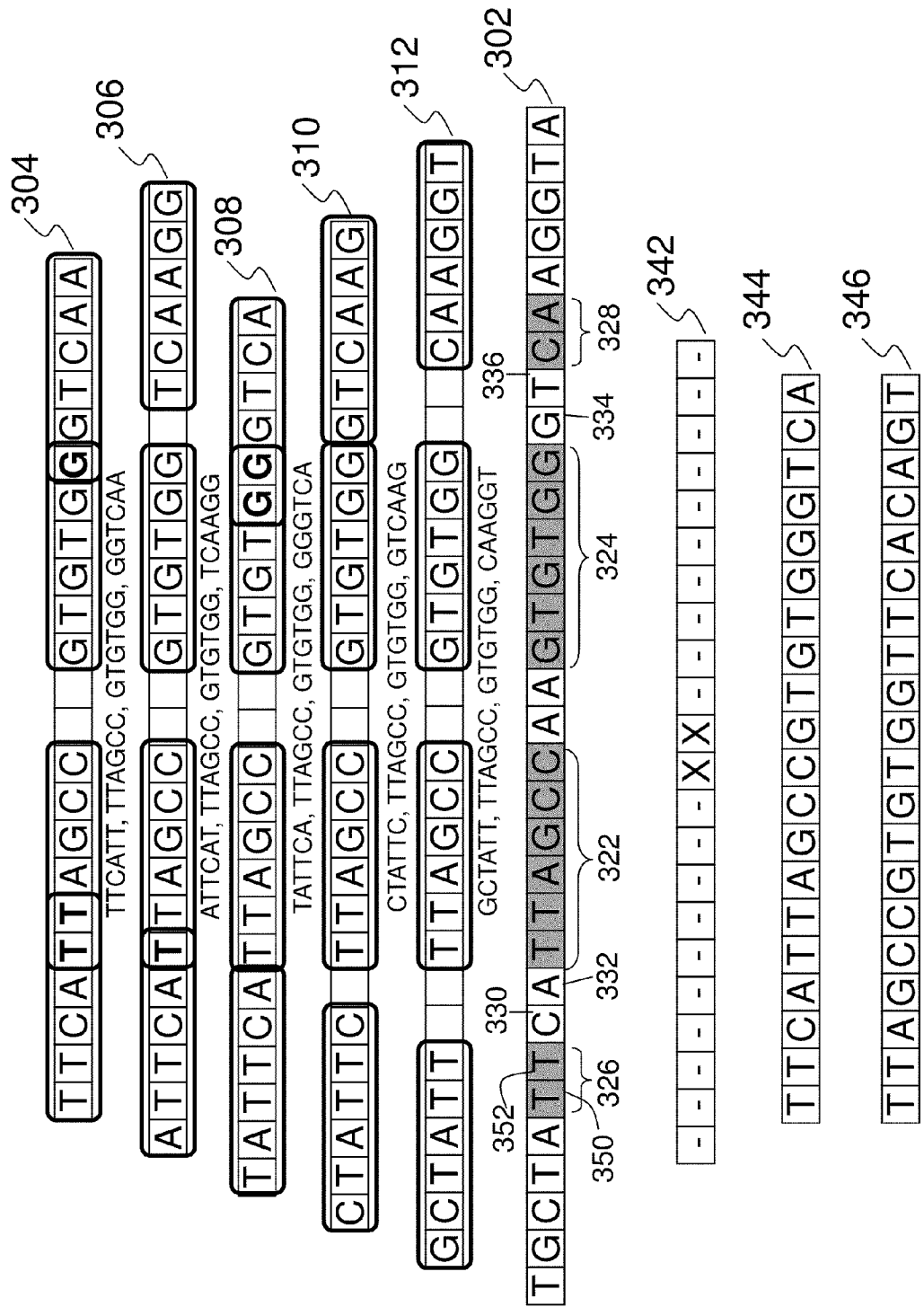
Figure 3C:
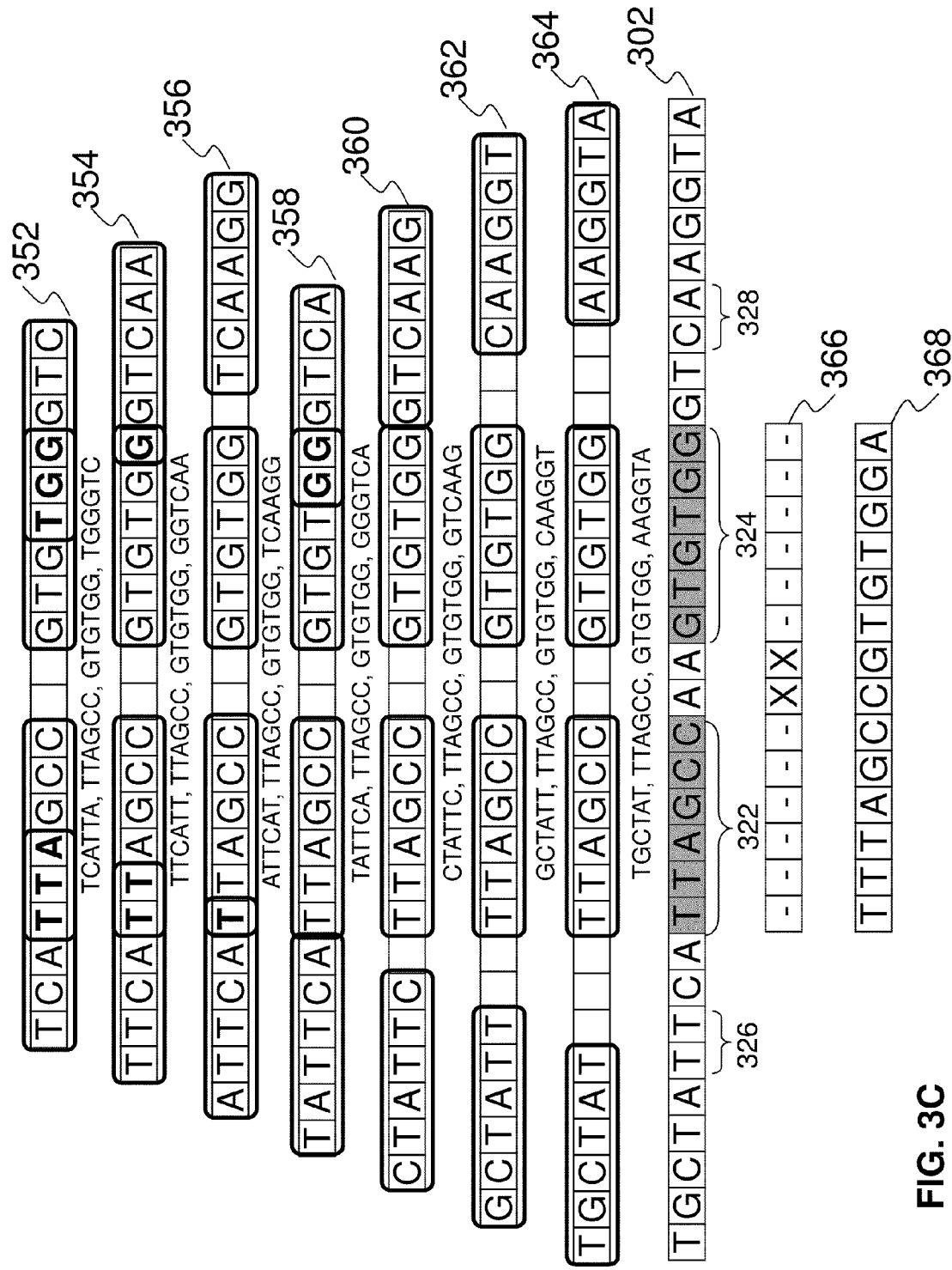

Different key indexes can be generated from a single reference by varying the bases included within the key pattern. For example, in FIG. 3B the key pattern 342 used includes four bases excluded in the key pattern 314 of FIG. 3A. The resulting keys 344, 346 are longer than they keys generated in FIG. 3A, which may be useful for certain mapping implementations. In FIG. 3C, a shorter key pattern 366 is applied to the reference to include only the bases with the highest match confidence to create keys (such as key 368) that can be used when using generated data sets with more variable spacing. Shorter keys, however, generally lead to identification of more potential locations in the reference, so the length of the keys should be balanced by the distribution of separation distances so as not to miss too many of the true mappings without producing an unwieldy number of low-specificity candidate matches.

FIG. 4A is an illustration of an index. In this example, each key-location pair is stored as an entry in index 400. The key strings are in lexical order. It is possible to have keys that correspond to more than one reference location as well as keys that do not correspond to any reference locations (the latter are omitted from the table in some embodiments). To look up a key in the index, a search (such as a linear, binary, or hashed search depending on implementation) based on the key string is performed.

Figure 4B:
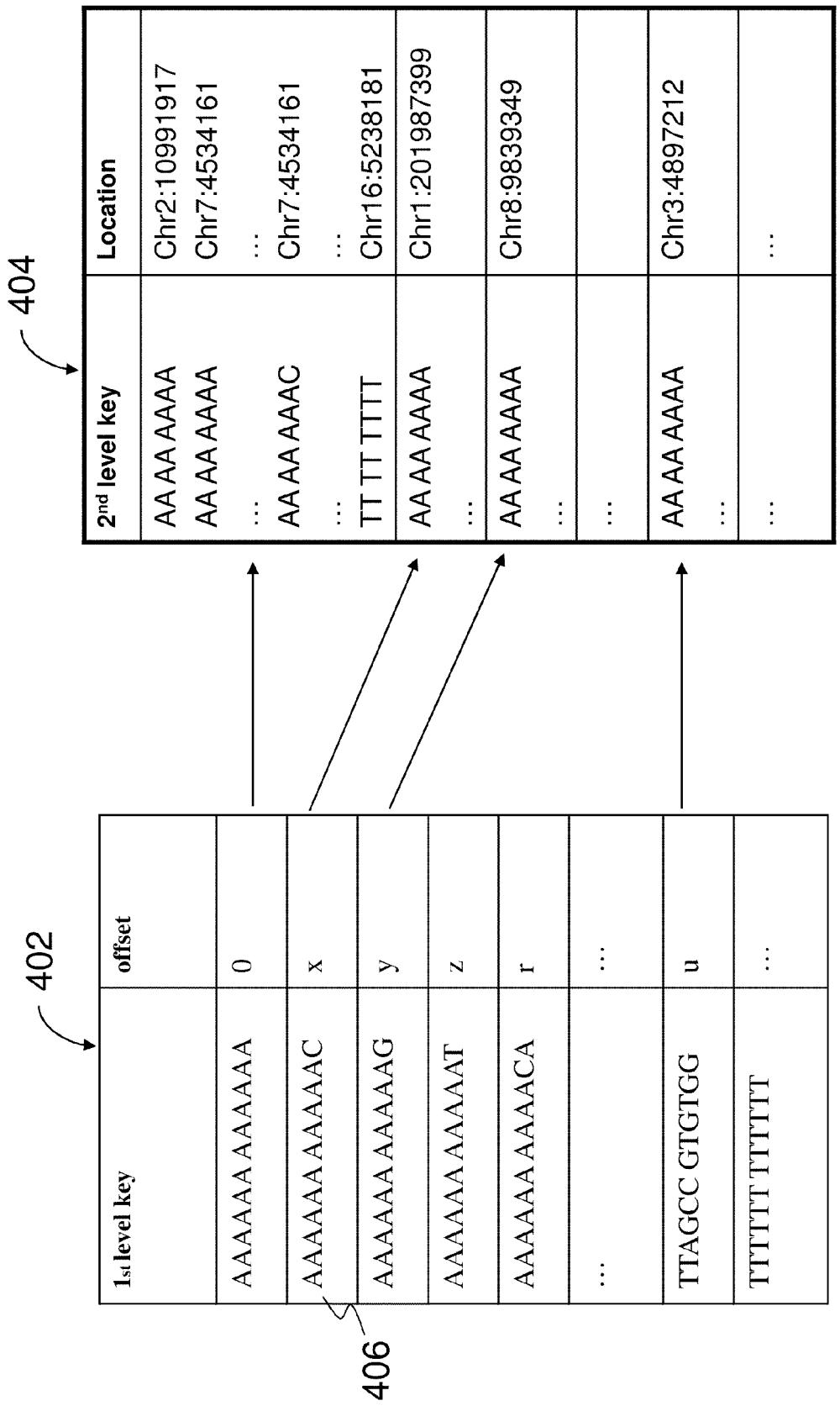
FIG. 4B illustrates another type of an index.

FIG. 4B illustrates another example of an index consisting of two levels or stages designed to increase lookup speed and reduce memory footprint. In this example, each key is split into two portions. The first portion is referred to as the prefix and the second portion is referred to as the suffix. The prefixes are stored according to their lexical order in a first sub-index 402, also referred to as a prefix table. The length of the prefix is chosen based on statistical probabilities, i.e., short enough so that nearly all sequence combinations of that length occur in the reference, and long enough so that the average number of occurrences for each sequence combination meets desired criteria. In this example, the prefix includes 12 bases. Given a prefix length, the length of the suffix depends on the pattern used to generate the key. For example, the suffix length is 4 for reordered keys generated using key pattern 314 (FIG. 3A), and 10 for key pattern 320 (FIG. 3B). The example shows a suffix length of 8. In the prefix table, each entry maps a prefix to an offset of a set of suffixes in a second sub-index 404, also referred to as the suffix table. Each set of suffixes include permutations of bases for the given suffix length. The offset is a value that represents or can be used to derive the base address of the set of suffixes relative to the address at the beginning of the suffix table. In the suffix table, each suffix maps to one or more corresponding reference locations that would generate the key that is the prefix/suffix combination. To find a location in the reference for a given key string, the prefix portion of the key string is identified in the prefix table to obtain the offset. The corresponding set of suffixes can be quickly located in the suffix table using the suffix table base address and the offset. The reference location can be found by looking up the suffix in the suffix set, e.g., by binary search. The suffix lookup is constrained not to exceed the starting location of the next set of suffixes. For example, given prefix 406, the search is restricted to a range between x and y.

Key Pattern Design and Derivation

The design of a key pattern can influence the efficiency, speed and/or computational cost of its use in index generation and mapping. In certain aspects, the oligomer sequences within a data set are individually too short to be used as effective keys on their own, as they will result in information on location that is not sufficiently specific. In other aspects, a longer key may be unnecessarily specific; this may result in an index that doesn't fit in available memory, or requires an excessive computational cost to avoid unacceptable sensitivity to sequencing error or variation between the reference and the sample being sequenced. The shorter the key used the less specific the sequence will be in a reference, and thus the more candidate locations that will be generated by the key. As a general rule, since these candidate locations need to be validated, having a greater number of initial candidate locations will require additional effort to be expended in the validation step. An acceptable key design is thus one in which an appropriate number of candidate locations are determined to allow for validation of these locations at a desired computational cost.

A key pattern may be derived from a corresponding set of oligomer sequence relationships. Examples of such oligomer sequence relationships include expected length(s) of the oligomers, the variation in separation or overlap distance (referred to as distance variation), the statistical distribution of the distance variations amongst oligomer sequences, and the statistical distribution of possible combinations of distance variations within sets of related oligomer sequences.

In some embodiments, the key patterns are derived by comparing possible arrangements of oligomer sequence sets according to the oligomer relationships, and finding conserved positions in the sequences. As will be shown in greater detail in the example below, bases located at the conserved positions can be determined with a high probability for any instantiation of a given set of oligomer sequence relationships. In what follows, we first consider positions which are absolutely conserved and then explain how this can be extended to handle various degrees of conservation. The probability of conservation of a base within a data set may be largely due to the nature of the biochemical process used to obtain the data set. Such information can inform the ordering of the key, as described in more detail herein.

FIG. 3A is a diagram illustrating an example of a key pattern derived from a set of oligomer sequence relationships. In this example, an arbitrary portion of a sample represented by sequence 302 is used to illustrate the key pattern derivation process described in 204 of process 200 (FIG. 2). The oligomer generation process divides the contiguous sequence 302 into a first portion of bases TGCTATTCATTAGCC, and a second portion of bases GTGTGGGTCAAGGTA. The two portions are separated by a fixed distance, in this case a distance of +2 (which are the two bases AA). For purposes of example, the following specification discusses in detail oligomer sequences that are six bases long (referred to as hexamers), although as discussed other oligomer sequence lengths are possible and in some instances preferable. In this example, the oligomer generation process yields two hexamers for each portion, giving a total of four hexamers, with the inner hexamers of each portion assumed to be positioned at the inner ends of the portions, hence separated by two bases (AA). The data generation process is such that the pair of adjacent hexamers obtained from the same sequence portion may have a variable separation or overlap distance, referred to as a distance variation. In this example, the two adjacent hexamers within each portion of 302 are said to have a distance variation of +/−2, which means that the hexamers may be separated by 1 or 2 bases (which corresponds to a distance of 1 or 2, respectively), overlap by 1 or 2 bases (which corresponds to a distance of −1 or −2, respectively), or abut each other without separation or overlap (which corresponds to a distance of 0). In other embodiments, the amount of distance variation may be different.

304-312 are various four-hexamer data sets illustrating the distance variations that may be generated by the biochemical process. As shown, in 304, hexamers TTCATT and TTAGCC have a distance of −2, and hexamers GTGTCG and GGTCAA have a distance of −1. In 306, hexamers ATTCAT and TTAGCC have a distance of −1, while GTGTGG and TCAAGG have a distance of +1. In 308, TATTCA and TTAGCC have a distance of 0 and GTGTGG and GGGTCA have a distance of −2. In 310, CTATTC and TTAGCC have a distance of +1, and GTGTGG and GTCAAG have a distance of 0. In 312, GCTATT and TTAGCC have a distance of 2, as do GTGTGG and CAAGGT.

A set of conserved positions that would make a reasonable key pattern can be determined by a comparison of these arrangements. Certain base positions in sequence 302 are included in the hexamers in any polyoligomer derived from the sequence with the inner two hexamers separated by the two bases AA and a variable data set distance variation of +/−2, regardless of which of the possible separation distance sets is utilized by a given polyoligomer. These conserved positions are shown as shaded regions in sequence 302. In this example, the conserved positions correspond to sequence portions 326, 322, 324, and 328 (TT, TTAGCC, GTGTGG, and CA), which appear in all the hexamer sets 304-312. For a given set of oligomer relationships, the conserved positions correspond to positions in a sequence that are determinable despite different distance variation between sequences. In other words, given a set of oligomer sequences generated from an unknown sequence using a specific (but variable) generation process, the bases of the sequence at the conserved positions will be determined with high probability.

One key pattern that is useful for such oligomer relationships is shown in 314, where the 16 conserved positions of the polyoligomer data set are shown as boxes containing a dash and the non-conserved positions (i.e., positions that cannot be easily determined based on a set of oligomer sequences) are shown as "x". Applying the key pattern to the portion of the reference shown at 302, beginning at position 350, produces key 316, which includes all the bases corresponding to the conserved positions, arranged in the same order as they appear in sequence 302. These bases can be rearranged based on additional probability of conservation to place the bases with the lowest probability of being unspecified in the data set at the beginning of the key string, as shown in key 318.

FIG. 3C is a diagram illustrating another example of a key pattern derived from another set of oligomer sequence relationships. In this example, the adjacent hexamers are known to have a distance variation of +/−3, which means that the hexamers may have a separation or an overlap of up to 3 bases. 352-364 show various possible arrangements of hexamers resulting from sequence 302, including an arrangement in which two adjacent hexamers overlap by 3 bases as shown in 352, and an arrangement in which two adjacent hexamers are separated by 3 bases as shown in 364. A comparison of these arrangements shows that while sequence portions 322 and 324 are still conserved (i.e., appearing in all hexamer arrangements) just as in FIG. 3A, sequence portions 326 and 328 are no longer conserved since the bases in these sequence portions do not appear in all the hexamer sets. The derived key pattern is shown as 364, where the conserved positions are again shown as boxes containing a dash and the non-conserved positions are shown as "x". In this example, key pattern 364 includes 12 conserved positions and is shorter than key pattern 314 of FIG. 3A.

Some tradeoffs exist among possible key patterns. Pattern 364 of FIG. 3C is more inclusive of the possible distance variations than pattern 314 as the former takes into account distances of +3 and −3. Pattern 364 is shorter than pattern 314 since fewer bases are conserved. An index generated based on a shorter pattern such as 364 would allow mapping of oligomer sequence sets with a distance of +3 or −3 to specific locations in the reference, while an index based on pattern 314 would not generally allow mapping in the naïve implementation (though see below). Thus, for a given collection of polyoligomer data sets, a shorter pattern accounting for a greater distance range and having fewer conserved bases leads to a higher portion of oligomer sequence sets being usable. In other words, a higher percentage of the oligomer sequence sets can be mapped to locations in the reference. On the other hand, pattern 364 includes fewer conserved positions than pattern 314 and results in shorter keys that are more likely to be mapped to multiple locations in the reference than a longer key. The identification of more candidate locations will require additional validation on an increased number of locations. Further processing is required in some embodiments to more accurately determine which of the multiple locations can be validated for a given data set, increasing computational cost. Thus, an effectively designed index takes into account these tradeoffs, and employs one or more key patterns designed to be both sufficiently long to avoid generating too many possible locations in the reference and sufficiently succinct to not rule out appropriate sequence relationships.

In some applications, the number of positions that is conserved in all possible instantiations of a polyoligomer dataset may not be enough to provide an acceptably-specific key. Thus, in certain implementations, the requirements for conserved positions are relaxed to obtain a longer key pattern such as key pattern 342 of FIG. 3B. In this example, included in key pattern 342 are bases at positions 330, 332, 334, and 336 (C, A, G, T, respectively), which only occur some of the time in various sets of oligomers. The corresponding sequence portions obtained by applying key pattern 342 to sequence 302 can be provided in the sequential base order of the reference, as in key 344, or attached towards the end of the key as in 346. In the naïve implementation, keys 344 and 346 allow some oligomer sets (such as 304 and 308) to be mapped but not others (such as 306, 310, and 312). It is also more likely for key 342 to map to a unique position in the reference than a shorter key such as 316 or 318. Related issues are discussed further in the following paragraphs.

In some embodiments, certain possible instantiations are simply excluded from the key pattern design as well as from mapping processes. Where statistical information regarding the frequency of various instantiations is available, it may be possible to determine a key pattern of acceptable specificity (length) at the expense of not covering an acceptably small fraction of datasets. For example, it may be that the possible distance variations between two oligomers are −3, −2, −1, 0, +1, +2, and +3. Without knowledge of the corresponding probabilities of occurrence, key pattern 364 shown in FIG. 3C, based on the maximum distance variation of +/−3 bases, might be selected. However, if the corresponding probabilities of occurrence are determined (by empirical measurements, by estimation, or by other techniques) to be 0.05%, 9.95%, 20%, 10%, 35%, and 24.95%, and 0.05%, possible sequence arrangements that have a distance of +3 or −3 might be disregarded, permitting a key pattern based on distance variation of +/−2. Thus, a key pattern 314 shown in FIG. 3A may be used for index generation and distance variations of +/−2 may be used for generation of keys from polyoligomers. In this case, those uncommon polyoligomer sets with a true distance of +3 or −3 will not be correctly instantiated and will fail to map or possibly be mapped incorrectly.

In other embodiments, the longer pattern is again used but instantiations resulting in ambiguous bases are accommodated by generating multiple keys, as described in more detail herein. This may be desirable if the use of the longer pattern without such accommodation results in too large a fraction of data sets not mapping. For those instantiations of a given polyoligomer which leave positions in the key pattern unspecified, bases may be selected based on data quality and/or statistical probability of base conservation, while in other implementations all possible completions of the pattern can be considered, as discussed herein. Examples of "ambiguous bases" includes bases in the data set which are not clearly one of the four expected bases for the data set, e.g., G, A, T, and C for DNA or G, A, U, and C for RNA. An ambiguous position includes an unidentified base, a base that is identified as two or more different bases for a single position in a data set, and the like.

Expanding ambiguous positions in this fashion can result in an exponential increase in compute cost. For this reason as well as others, in some embodiments the bases of a key pattern may be reordered in constructing a key. Some of the possible motivations are as follows.

In the situation just discussed, where the allowed separation distances are such that some portions of a key pattern may be unknown, if the bases selected by the key pattern are reordered to form the final key so that the unknown bases are the last bases of the key (or the least significant bits in terms of index lookup), and the index lookup mechanism is appropriate it is possible to avoid explicit enumeration of the possible completions. In specific situations, the key is effectively shorter (less specific), but only for those instantiations that result in incomplete specification of the key. Even if the goal of placing the unknown bases at the end of the key is not fully realized, a design in which the missing bases affect later positions (lower-order bits) of the key results in better memory locality (improved cache behavior). These situations can be illustrated by FIG. 3A, if we assume that distances of +3 and −3 bases will be considered in generating keys from polyoligomers, but are disregarded when deriving the key pattern. Pattern 314 of FIG. 3A is chosen in this example. Sequence groups 322 (TTAGCC) and 324 (GTGTGG) are more likely to appear in the oligomers since their locations are fixed and do not depend on the distance variation between oligomers. In comparison, sequence groups 326 (TT) and 328 (CA) are less likely to appear because these sequence groups appear in oligomer sequence sets if the distance variation is within +/−2 bases but do not always appear if the distance is +3 or −3 bases. Thus, key 318 is generated, with sequence groups 322 and 324 placed at the beginning of the key, and sequence groups 326 and 328 appended after portions 322 and 324 in the key since groups 322 and 324 are more likely to appear in keys derived from sequence sets than 326 and 328. When using the resulting index to map a polyoligomer with separation distances allowed to range over +/−3, some bases of the key will be unspecified in some instantiations of the polyoligomer. For certain instantiations (in the example, separation distance within +/−2 on the left, and separation distance −3 on the right), the unspecified base is the last base of the key, so we do not need to enumerate the possible values. In others, one or two of the final four bases of the key may be unspecified. Due to reordering, the first twelve bases of the key will always be determined by the inner hexamers, hence retaining better specificity in the former approach and yielding better locality of multiple index lookups in the latter.

In some embodiments, reordering the bases of the key may have additional advantages even when all positions within the key are specified in all allowed separation relationships. A plurality of different keys for a single polyoligomer set may be obtained from a single key pattern, corresponding to instantiation with different possible separation relationships. Even where all bases of the key pattern are specified in all keys, certain bases of the pattern are modified less than others. If the bases of the key pattern are reordered to place the more-constant bases first in the key, better locality (cache performance) can be achieved across the set of index lookups for a given data set. This can be illustrated by FIG. 3A. Due to the requirement that the inner two hexamers be separated by precisely two bases, the same twelve bases can be made to occupy the same positions in all keys derived from a single polyoligomer. Reordering the bases of key pattern 314 such that segments 322 and 324 are placed at the beginning of the key, so that sequence 302 gives rise to key 318, is an illustration of this concept. In some embodiments, this is taken further; keys are generated from a single data set and key pattern by examining sequence relationships in an order that improves locality among index lookups. By enumerating sequence relationship possibilities in certain orders, the more significant bits of the keys change less often. Referring to FIG. 3A, if the final order of bases in the key for sequence 302 is 322+324+326+328, giving rise to keys such as 318, e.g., it will be preferable to enumerate the possible separation relationships for a polyoligomer data set by considering all possible separations of the oligomers in the right portion together for each possible separation within the left portion; this will lead to considering all keys sharing the first 14 bases in a group. Whereas, inverting the process to consider all possible separations of the left portion together for each possible separation of the right portion will lead to considering keys sharing the first 12 and the last 2 bases in a group. For some embodiments of the reference index, the former will give better locality.

Oligomer Sequence Mapping

Figure 5:
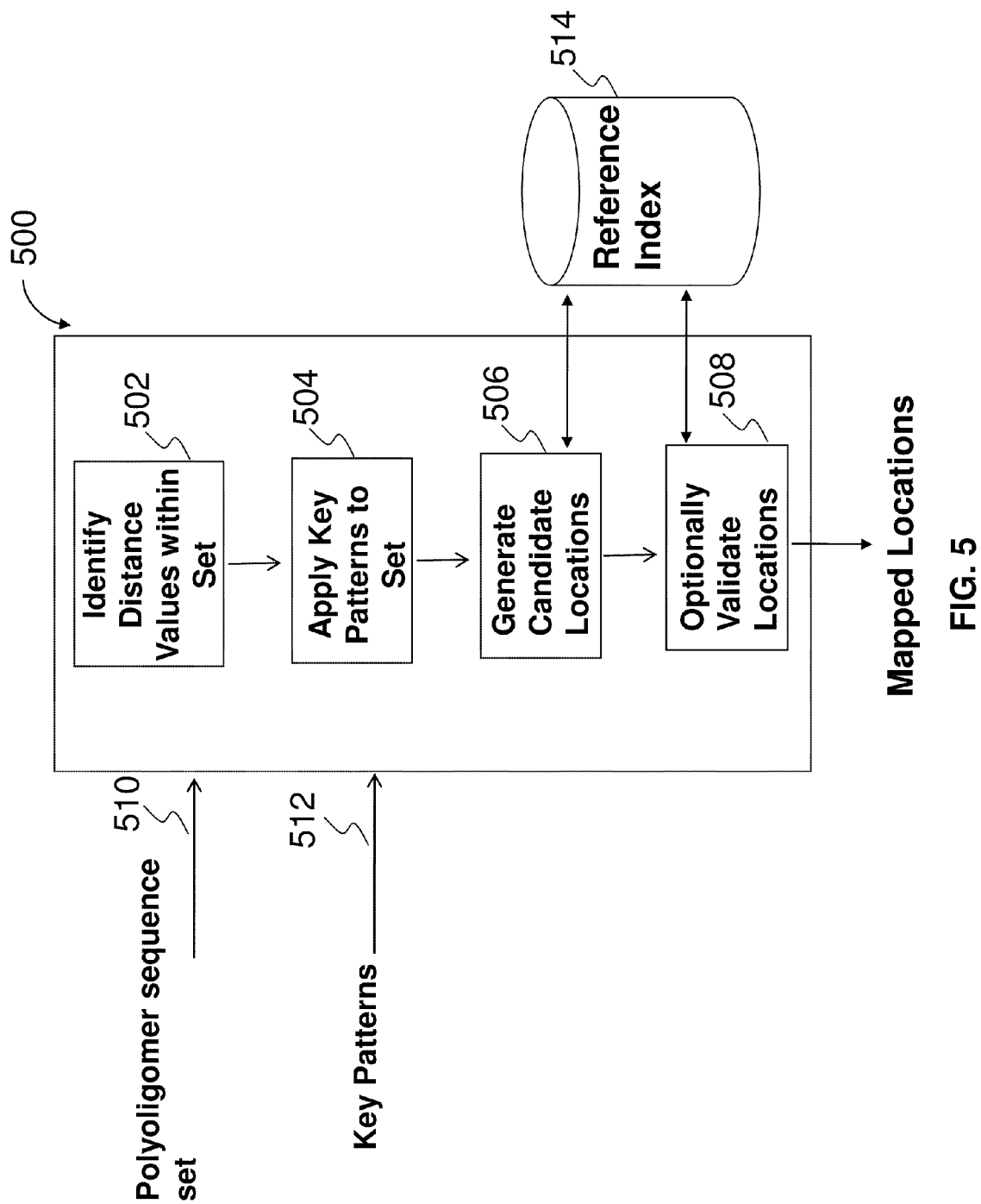
FIG. 5 is a flowchart illustrating an implementation of a process for mapping oligomer sequences.

Once an index is generated, it can be used to map oligomer sequences obtained from samples using the key patterns used to produce the index. FIG. 5 is a flowchart illustrating an implementation of a process for mapping oligomer sequences. Process 500 may be implemented on an oligomer mapping system such as that illustrated in FIG. 1 at 100. At 502, a data set of related oligomer sequences (510) are received. At 504, one or more key patterns (512) derived from a set of oligomer relationships are applied to a polyoligomer data set to obtain one or more keys that are consistent with the data set. The one or more keys are located (506) in a reference index (514) configured to map possible keys to their respective candidate locations in the reference. The reference index may be generated as illustrated in FIG. 2. The identified candidate locations are optionally validated (508), either using the index (514) as shown, or through other means. For example, the candidate locations can be validated by comparing the sequence at a candidate location of the reference to possible instantiations of the complete sequences of the polyoligomer. The successfully mapped location(s) are optionally output and may be used for genetic analysis, subsequent software processing, and many other applications. For example, the location(s) are used in some embodiments to assemble a new sequence/genome assembly. In some embodiments, the locations are used to detect novel sequences.

Figure 6:
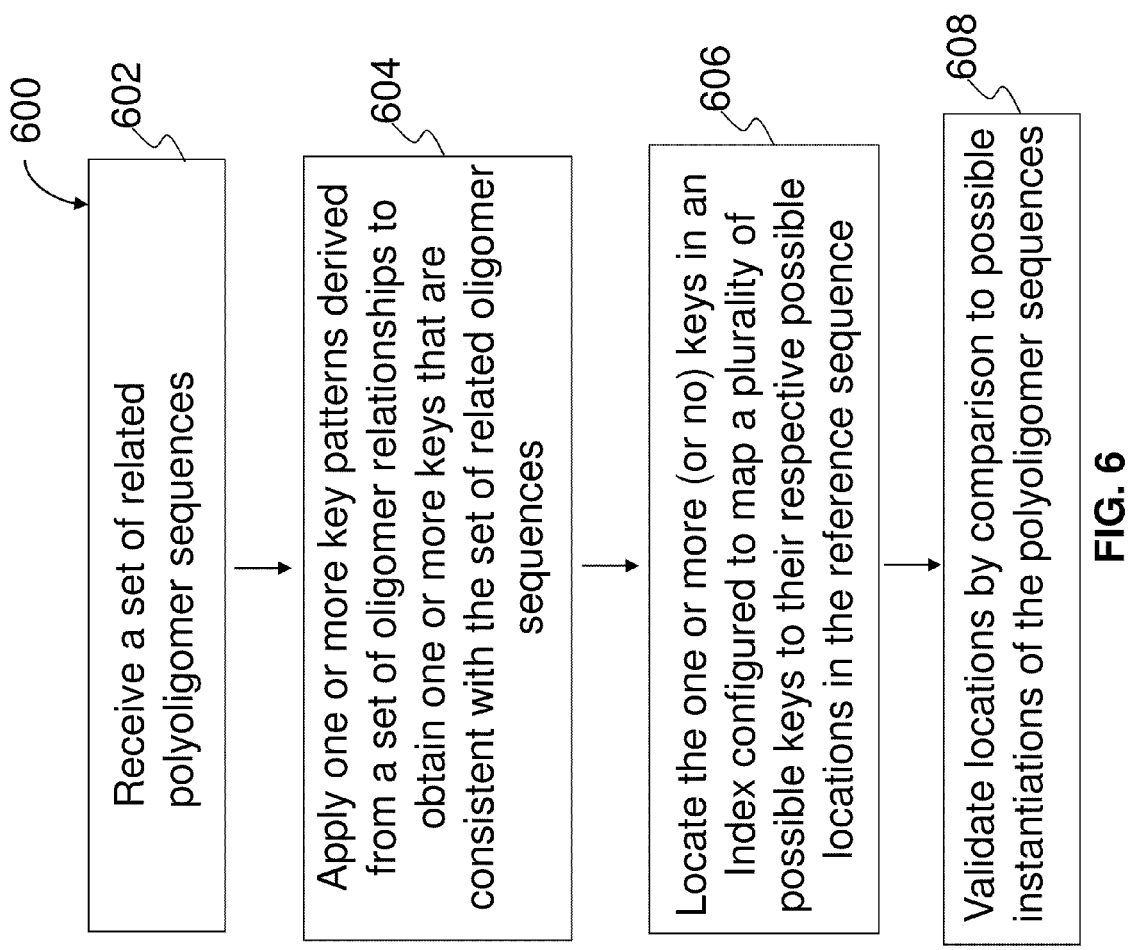
FIG. 6 is a flowchart illustrating a process for obtaining keys that are consistent with a given set of related oligomer sequences.

FIG. 6 is a flowchart illustrating an implementation of a process for obtaining keys that are consistent with a given set of related oligomer sequences. In some embodiments, process 600 is used to implement process 500 (FIG. 5). At 602, one or more distance values that could have existed between at least some of the given set of oligomer sequences are selected. At 604, these possible distance values are used to instantiate the data set. One or more key patterns, based on the inputs of the sequence set 610 and the reference 608, are applied to these possible instantiated sequences with the selected distance values to obtain one or more corresponding keys. These keys can be compared to those in the appropriate index 606 to identify possible locations.

Figure 7:
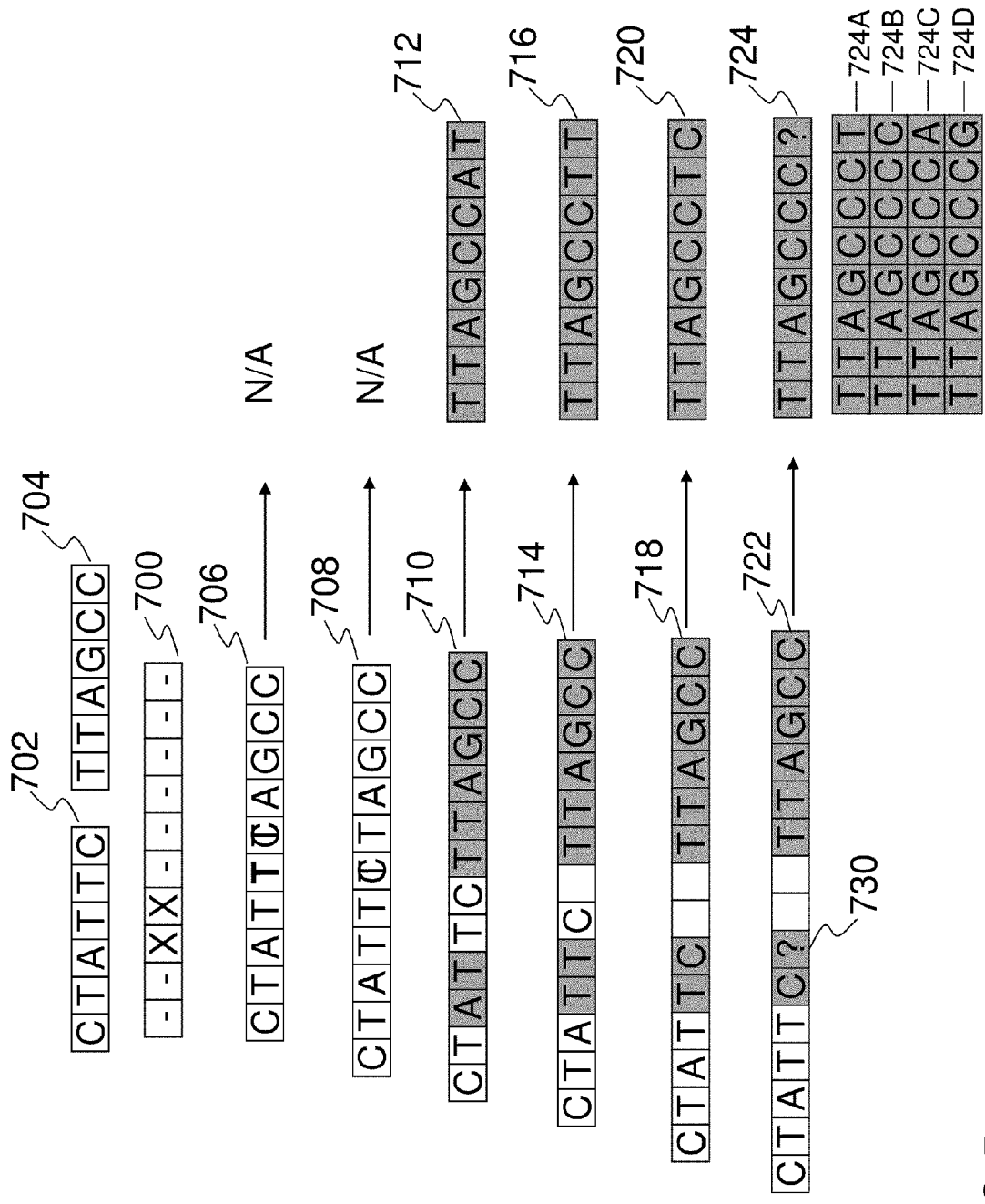
FIG. 7 is a sequence diagram illustrating an example of obtaining keys that are consistent with a given set of related oligomer sequences, using a process similar to 600.

FIG. 7 is a sequence diagram illustrating an example of obtaining keys that are consistent with a given set of related oligomer sequences, using a process similar to 600. For purposes of illustration, the example shows a partial key pattern 700 and a partial set of two adjacent, related hexamers 702 and 704. A complete key pattern and a full set of related oligomers are used in practice. Here, key pattern 700 includes 2 conserved positions, followed by 2 non-conserved positions, followed by 6 conserved positions. Furthermore, the last base of the pattern is constrained to correspond to the last base of the second hexamer. Selective distance values and possible sequences are evaluated to determine whether hexamers 702 and 704 can be generated from such sequences. 706 shows the two hexamers overlapping by two bases. Since the end of hexamers 702 and the beginning of 704 (TC and TT, respectively) do not match perfectly when overlapped by 2, it is impossible for the distance between the hexamers to be −2, unless there is an error in the data set in one of the two conflicting bases. Had the end of hexamer 702 been TT instead of TC, a distance of −2 would have been feasible. 708 shows that it is also impossible for the distance to be −1 due to the mismatched end bases (C for 702 and T for 704). It is possible, however, for the hexamers to have a distance of 0, 1, 2, or 3 and forming sequences 710, 712, 718, and 722, respectively. The instantiations from the data set can then be reordered to place the bases with the lower quality scores at the back of the key, forming reordered keys 712, 716, 720, and 724. Due to the fact that sequence 722 has one unknown position, there are four potential instantiations for 724, one with each of the four bases at the unknown position. Thus, this instantiation is either disallowed or the missing position is filled in with all possible values to create substituted keys, as shown in 724A-D. Locations in the reference can be looked up in the index using these keys.

In some embodiments, statistical distribution information about distance combinations within a set of related oligomer sequences can be used to limit computation. The information is used to include or exclude certain instantiations of a data set. For example, if it is known that when there is a distance of +1 between the first pair of oligomers, there is a 99.9% chance that there is a distance of 0 between the second pair of oligomers, sequence arrangements assigning a distance of +1 between the first pair and a non-zero distance to the second pair could therefore be omitted for the purpose of deriving keys from each data set.

Figure 8A:
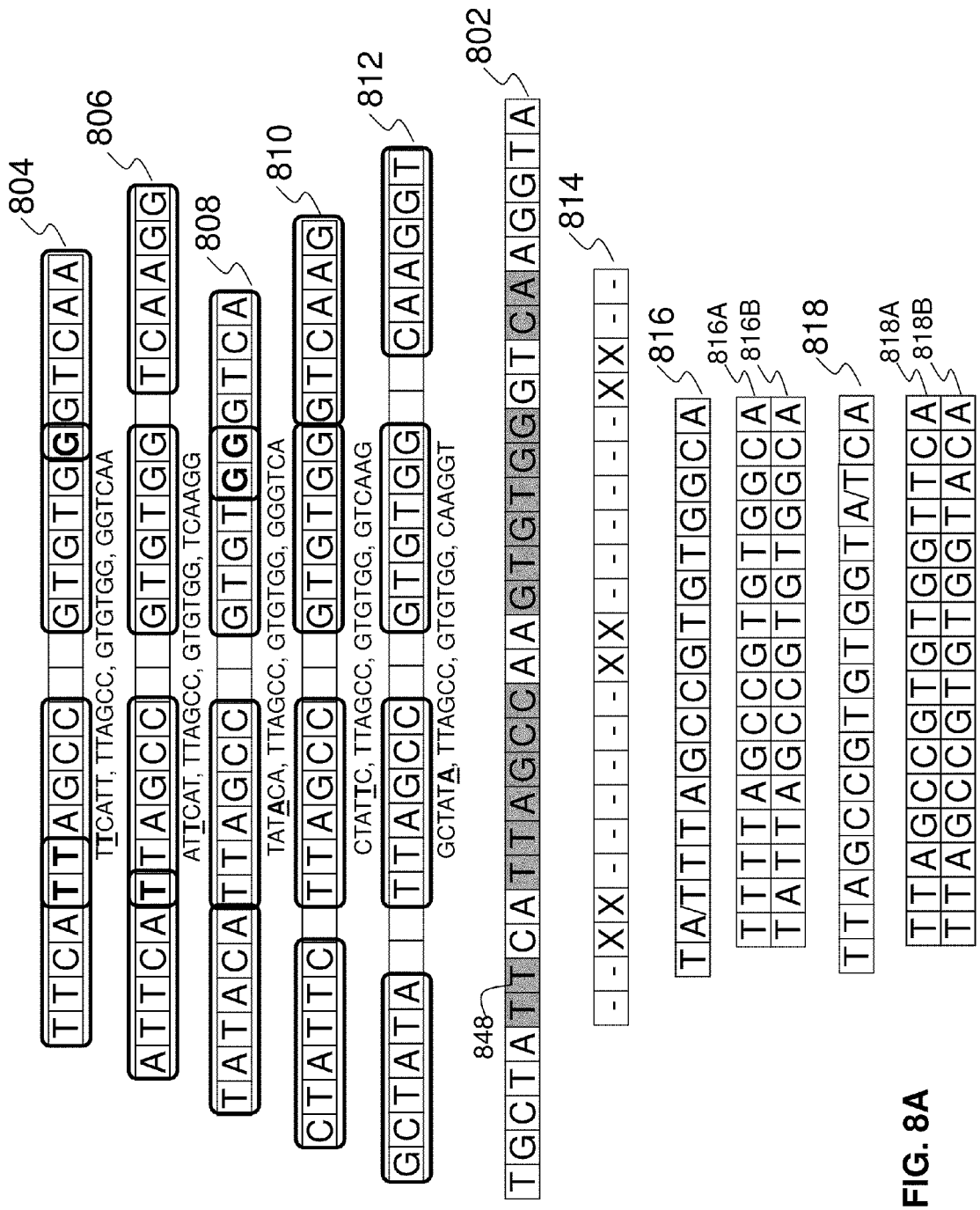
FIGS. 8A-8E are diagrams illustrating examples of keys generation using key patterns and substitutions or deletion of ambiguous positions.

In other embodiments, obtained polyoligomer data sets corresponding to the same mapping region may have one or more positions in the oligomer sets that are not clear data points, referred to herein as "ambiguous" bases or positions, such as those illustrated in FIGS. 8A through 8E. In FIG. 8A, a polyoligomer data set having sets 802, 804, 806, 808 and 812, which are all individually complete oligomers. Although these bases should have consistently conserved positions when key 814 is applied, as in FIG. 3A, here there is a discrepancy between the data sets, with sets 804, 806 and 810 having a "T" at position 848 in the reference, and sets 808 and 812 having an "A" at position 848. Instead of searching the index for a key with a base missing, as illustrated in sequential key 816 and reordered key 818, the mapping operation can be carried out for each of the two potential variations, A and T, as shown in substituted sequential keys 816A and 816B and substituted reordered keys 818A and 818B.

Figure 8B:
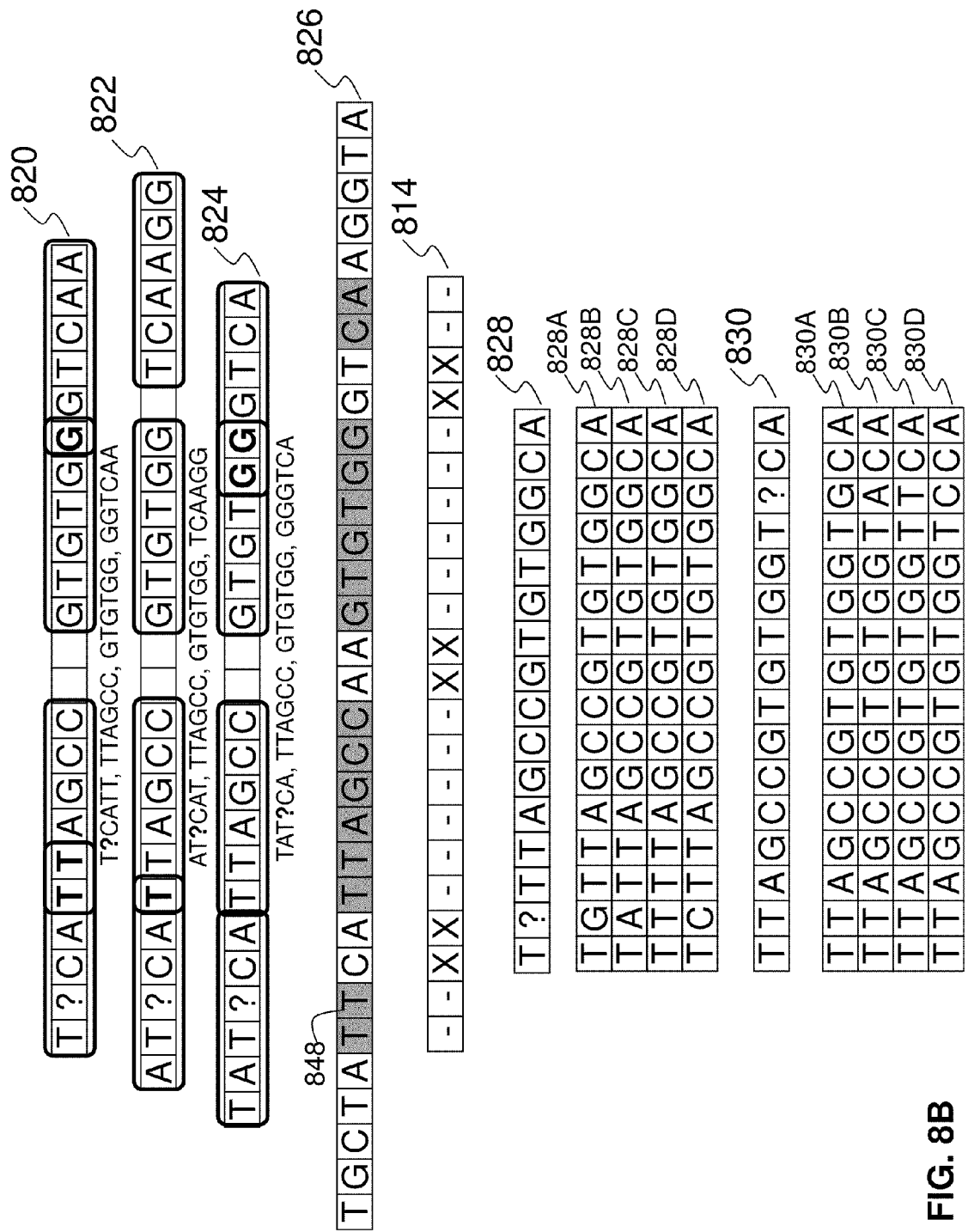

In other examples, an unidentified position may be substituted with each of the potential bases, resulting in four possible keys for each unidentified position in a polyoligomer data set. FIG. 8B illustrates a scenario in which position 848 in the obtained polyoligomer data sets is completely unidentified, and therefore may be any of the four bases. The key 814 applied to these data sets results in a key of 16 bases, with 14 contiguous bases and one unknown base, illustrated as sequential key 828 and reordered key 830. Rather than use only the 14 contiguous bases to map the data in the index, the index may be searched in four separate operations using the keys 828A-D or 830A-D, which respectively correspond to substituted keys having 16 contiguous bases that represent all of the possible combinations of the unidentified base in the initial key.

Figure 8C:
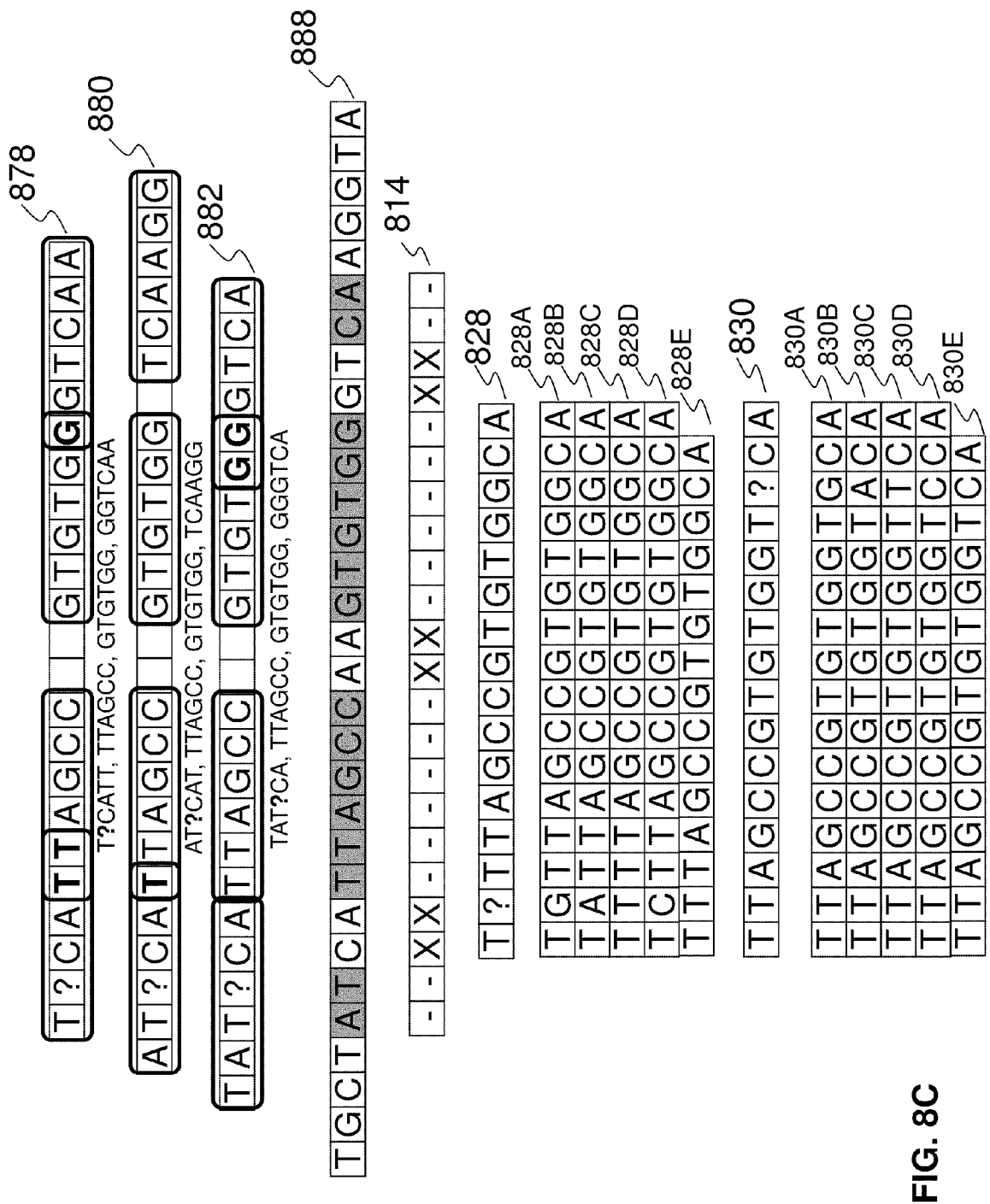

In specific examples, the data set may actually have an indel, such as the one base insertion shown in the data set in FIG. 8C. The data sets 878, 880 and 882 have an additional, ambiguous base compared to reference sequence 888. In such a case, to address the possibility that there is an insertion in the test sequence, a fifth key permutation from the polyoligomer data sets—sequential key 828E or reordered key 830E—could optionally be used alone or in combination with the other four predicted keys to map the obtained key to the reference. In such cases, the key 828E or 830E will have fifteen contiguous data points, and the unidentified base will be treated as if non-existent for mapping purposes. Alternatively, if multiple data sets share an absent base or additional base in the same position, the keys can be redesigned and/or the index adjusted to reflect the divergence of the data sets from the reference.

Figure 8D:
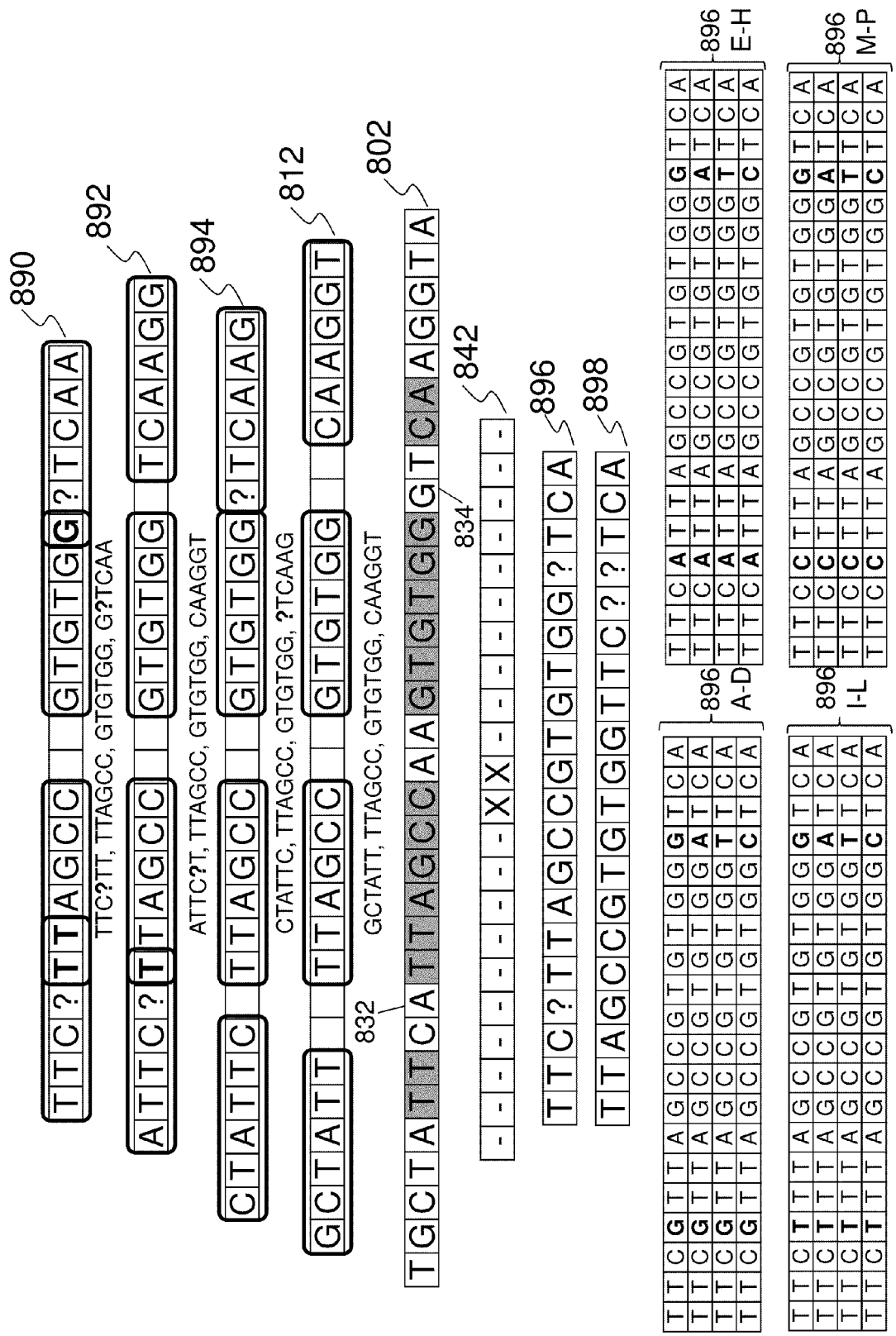
Figure 8E:
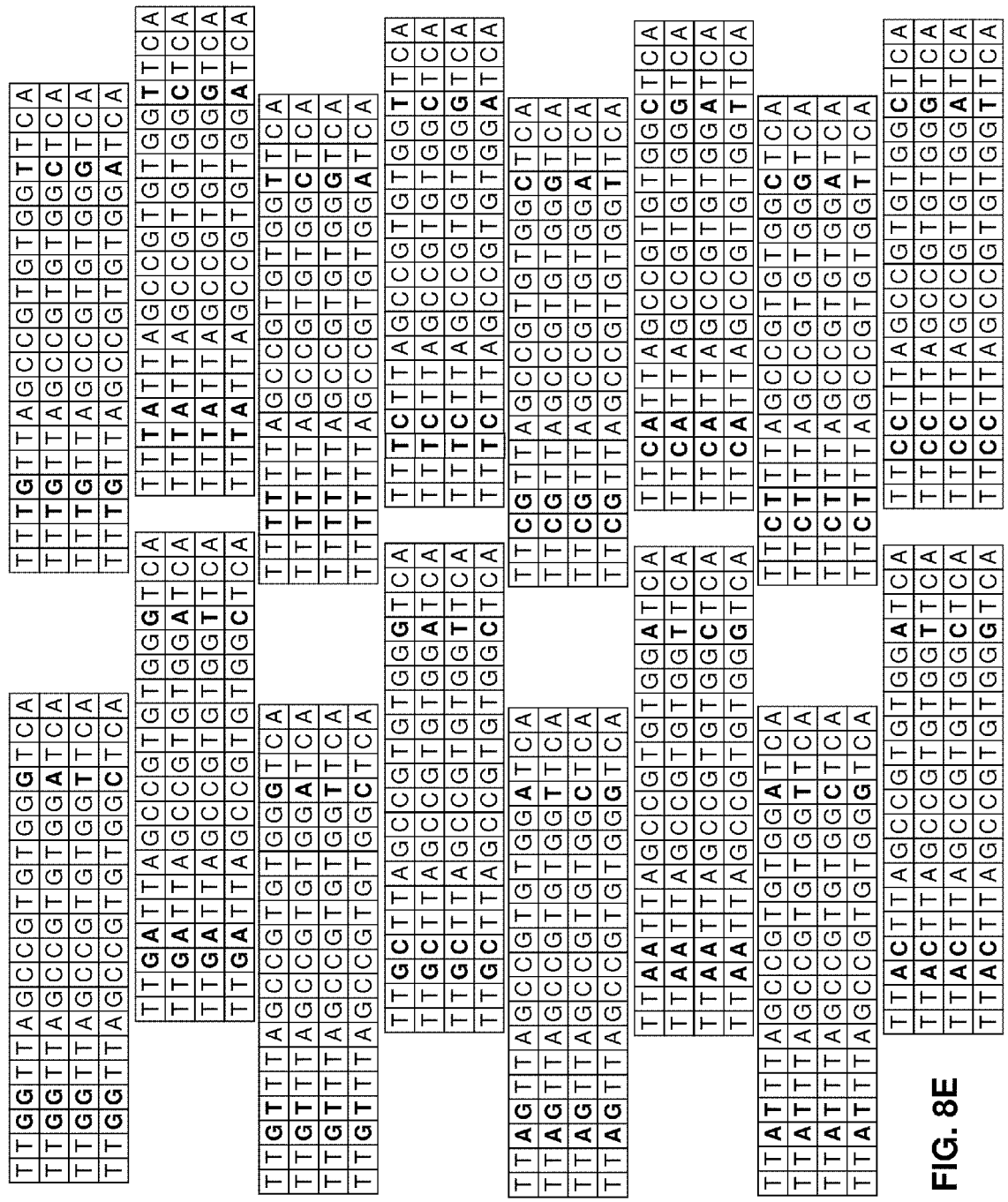

The use of multiple predicted keys generated from a polyoligomer data set to map potential locations in a reference index can be used to map data sets having two or more ambiguous or unidentified bases within a single data set. FIGS. 8D and 8E illustrate the use of multiple keys that may be generated from polyoligomer data sets having two unidentified bases when key pattern 842 is applied to the data set (890, 892, 894 and 812). In this example, application of key pattern 842 results in two unidentified bases at positions 832 and 834 in reference 802. When key pattern 842 is applied to the polyoligomer data set, the initial keys that are generated have two unidentified positions, as shown in sequential key 896 and reordered key 898.

With multiple unidentified positions in a key, there are $4^n$ different potential keys that could be used to map the data set in an index, with n=the number of unidentified positions. The use of a large number of instantiations will need to be balanced against computer cost, likelihood for ambiguous or incorrect mapping data or technical cost for re-obtaining the data sets. In certain circumstances, it may be preferable to search the multiple keys, and FIG. 8D illustrates the sequential keys 896 A-P that would be generated for two unidentified positions using key pattern 842, with each of the variable positions highlighted in bold. FIG. 8E illustrates the potential permutations if an additional third position were ambiguous, with a total of three unidentified bases in the initial key. This would result in $4^3$ or 64 possible substituted keys, which are set forth in 8E with the variable positions highlighted in bold.

Figure 9A:
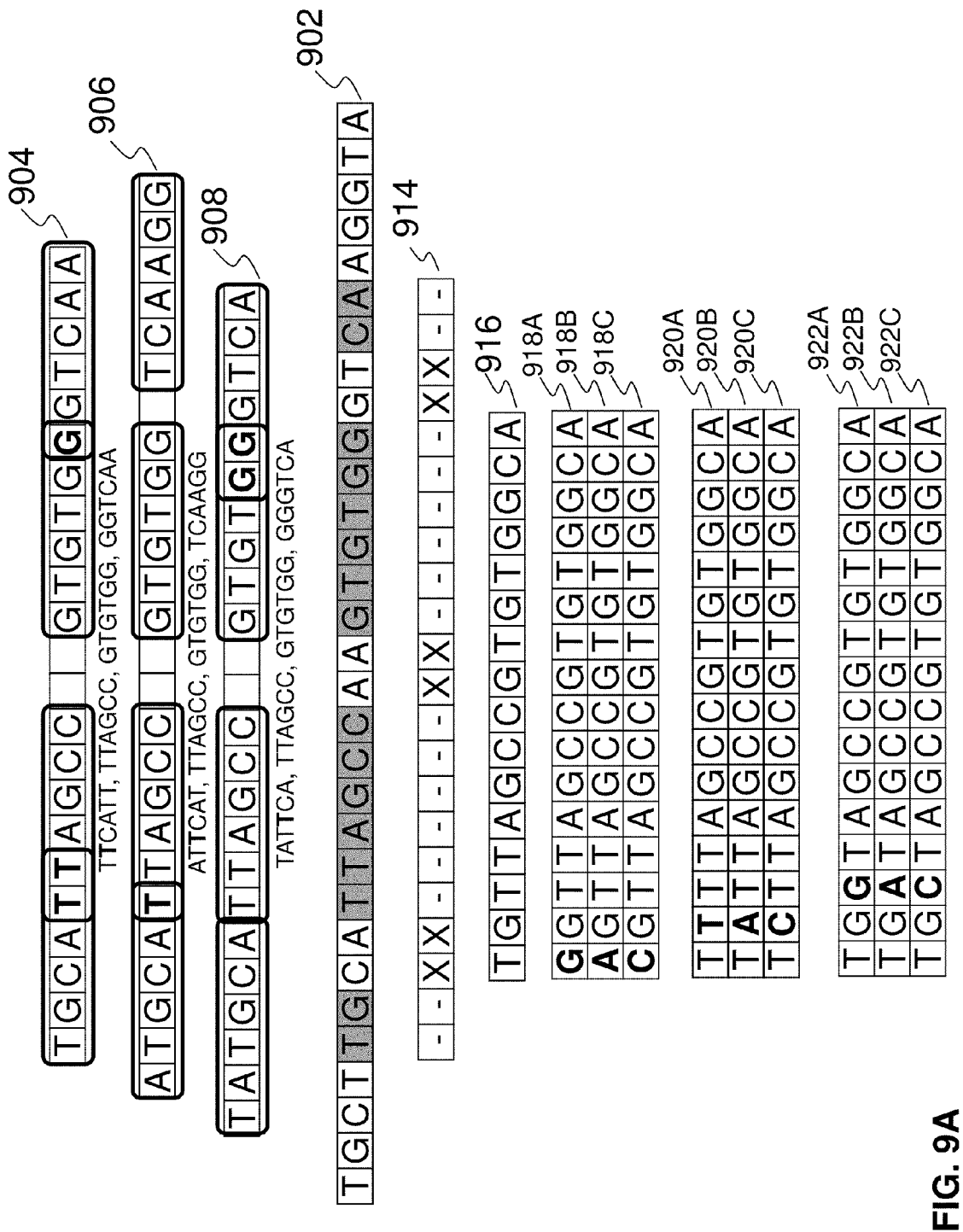
FIGS. 9A-9D are diagrams illustrating base substitution approaches of specific implementations of the invention.

In specific implementations of the invention, one or more positions in a key, and preferably the majority or all of the positions in a key, are singly substituted to reflect each of the possible bases at the substituted positions. In FIG. 9A, individual positions within a key are systematically substituted to reflect each of the four DNA bases. In this example, the initial generated key (916) is substituted one position at a time with each of the other three bases. This is shown for the first three positions of the key, although it is intended that this implementation would include a similar substitution at the majority or all of the positions within the key. The first position "T" in the key is substituted with a G, C, or A to create substituted keys 918A-C. The second position "G" in the key is substituted with a T, C, or A to create substituted keys 920A-C. The third position "T" in the in the key is substituted with a G, C, or A to create substituted keys 922A-C, and so forth.

Substitution of pairs or multiple bases may be preferable to substitution of individual bases in certain circumstances, although the amount of additional computation necessary for these more complex operations and the associated computing cost may limit its use in certain circumstances. Thus, in specific implementations, substitution of specific base pairs, triplets or multiple base units can be used in conjunction with individual position base substitution to confirm sequences in the data sets that are divergent from the reference.

In combined base substitution implementations, the key positions are substituted as combinations of two or more bases. Although it is explicitly intended that substitution of three or more base combinations be included in the scope of the invention, the examples presented in 9B-D illustrate the concept with pairs so as not to complicate or obscure the novelty of these implementations. This in no way is meant to limit the scope of the invention to such pairs, and it is intended that the invention also include simultaneous substitutions of three or more positions within a key.

Figure 9B:
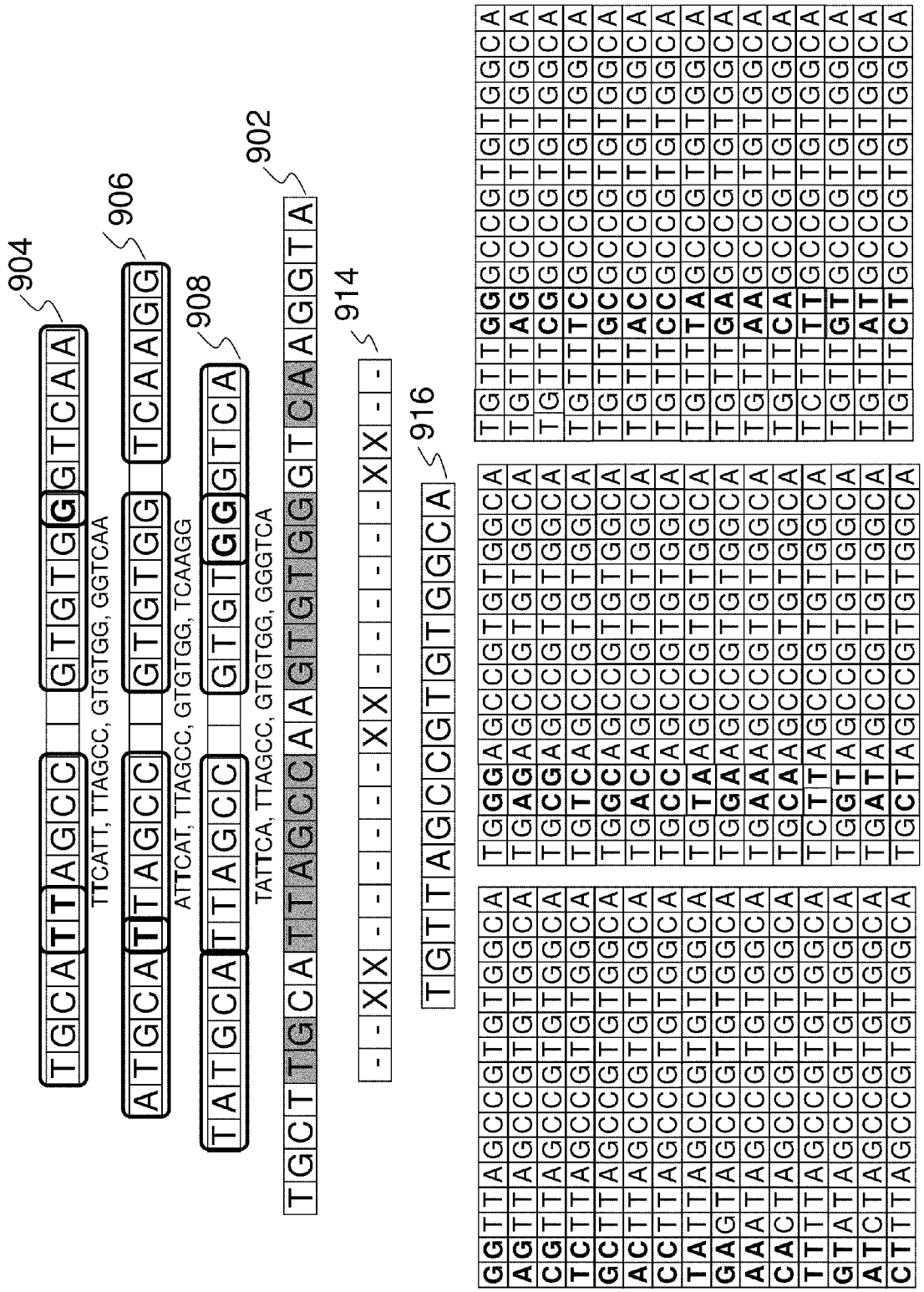

FIG. 9B shows substitution of adjacent pairs of bases in the key to create a set of substituted keys representing all possible combinations of these pairs in the key. Here, the substitution is performed sequentially at adjacent base pairs: the first substitution is for positions 1-2 of the key (916), substituting all possible combinations for the initially generated pair "TG". The remaining positions of the key (916) remain as in the initially generated key. The next combined position substitution is for positions 3-4 of the key (916), the initially generated pair "TT". The third combined position substitution is for positions 5-6 of the key, the initially generated pair "AG", and so on. The position pairs are preferably substituted for each adjacent pair within the initially generated key.

Figure 9C:
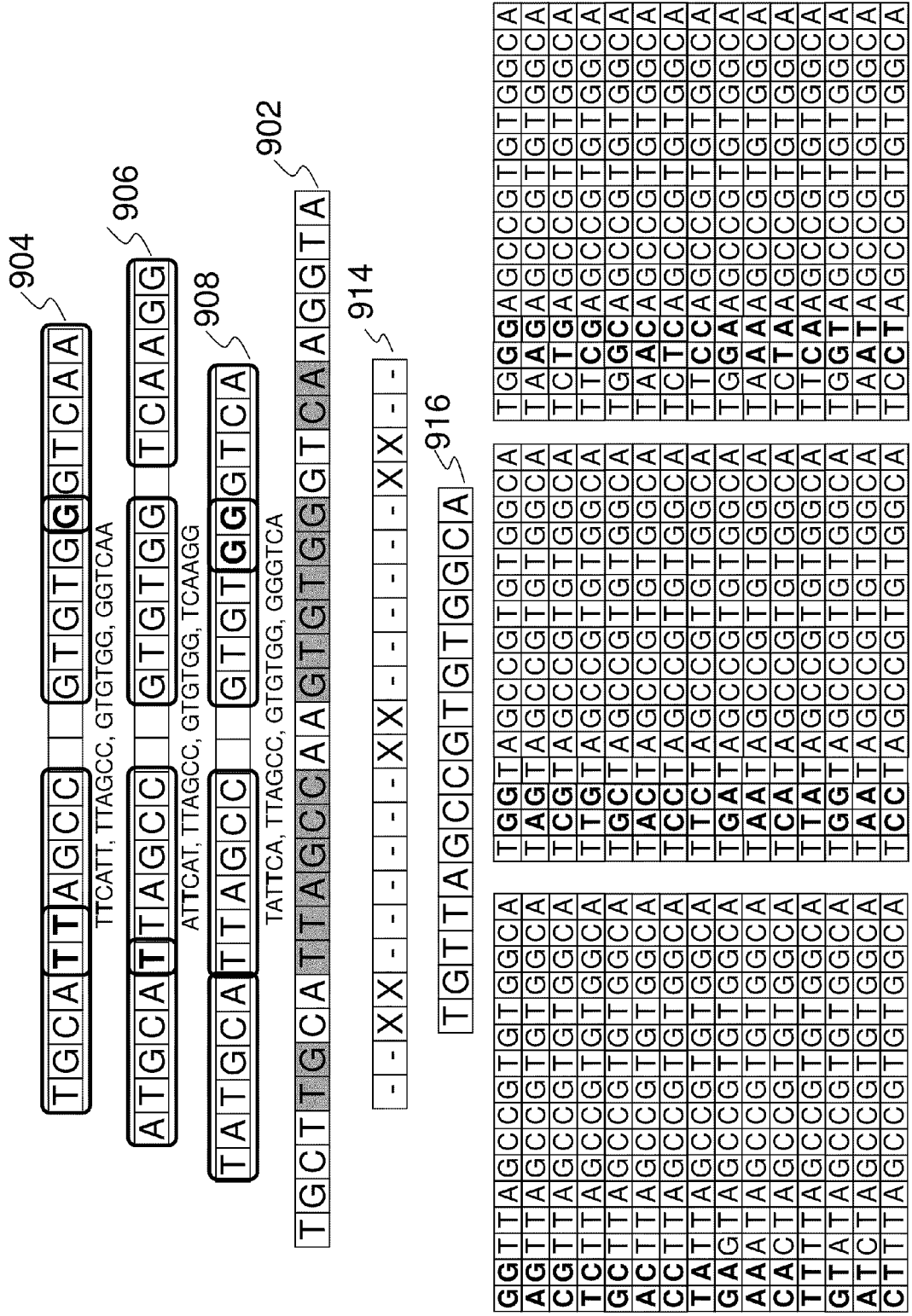

FIG. 9C shows the sequential substitution of overlapping base pairs to create a set of substituted keys representing all possible combinations of these pairs in the key. Here, the substitution is performed on overlapping base pairs: the first substitution is for positions 1-2 of the key, substituting all possible combinations for the initially generated pair "TG". The remaining positions of the key (916) remain as in the initially generated key. The next substitution is for positions 2-3 of the key (916), the initially generated pair "GT". The third substitution is for positions 3-4 of the key (916), the initially generated "TT" and so on. This operation would require more substitutions to cover the different base pair combinations for the initial key compared with the operation described in FIG. 9B, and thus would require more computing effort and cost; however, it is useful in certain circumstances to provide a higher degree of confidence in the mapping of data set sequences that have sequence differences from a reference sequence, e.g., point mutations, indels, and polymorphisms.

Figure 9D:
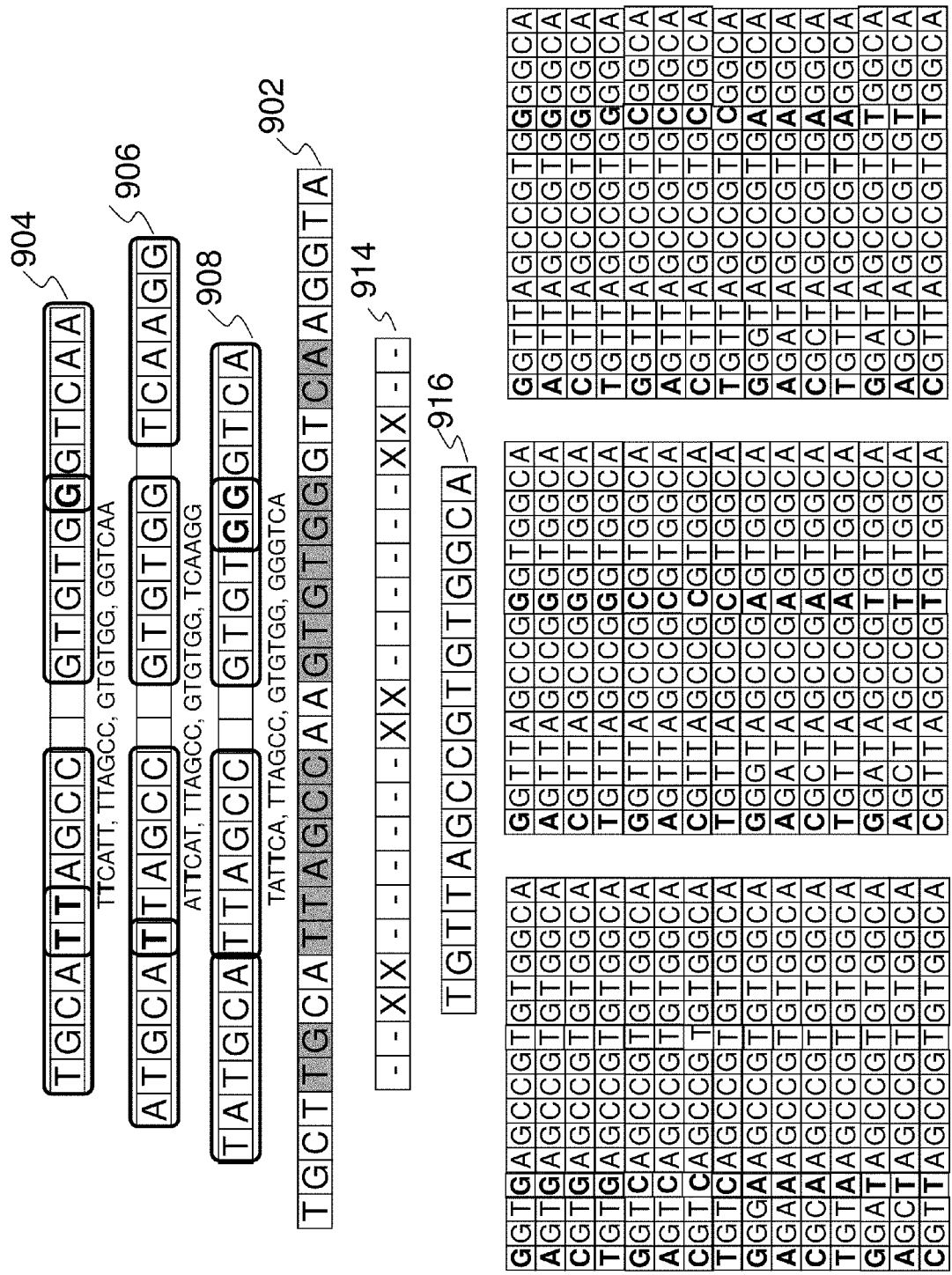

FIG. 9D shows the substitution of selected non-adjacent pairs of bases within a key. These bases may be selected based on a number of criteria, including quality score, the consistency of base conservation within multiple data sets, and the like. The substitutions are in non-adjacent bases, and the combined base substitutions do not necessarily include a substitution of every base within the key. Such operations may be useful, especially in conjunction with other operations such as individual substitutions of each position or base pair substitutions that involved each of the positions within the key.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of oligomer sequence mapping, the method comprising:
   receiving a data set of related oligomer sequences obtained from a same fragment of genetic material;
   receiving a key pattern corresponding to a reference index;
   receiving the reference index, the reference index generated by respectively applying the key pattern to each of a plurality of locations of a reference sequence to obtain a plurality of reference keys, the application of the key pattern to each of the locations selecting a same number of specified positions of the reference sequence, wherein the reference index includes the reference keys ordered by bases at one or more positions in the reference keys, the reference keys of the reference index being a same length;
   applying the key pattern to the oligomer sequences in the data set to generate a first key comprising selected positions of the oligomer sequences;
   modifying one or more bases at one or more positions of the first key to create a set of one or more modified first keys; and
   comparing the modified first keys to the reference keys in the reference index to identify one or more reference keys that match to one or more of the modified first keys, thereby determining one or more candidate locations of the oligomer sequences in the reference sequence, wherein the method is performed with a computer.

2. The method of claim 1, wherein the one or more bases at the one or more positions are modified in the data set prior to application of the key pattern.

3. The method of claim 1, wherein the one or more bases at the one or more positions are modified following application of the key pattern.

4. The method of claim 1, further comprising:
   validating candidate locations by comparing all bases of the data set to the indicated portions of the reference sequence corresponding to the matching reference keys.

5. The method of claim 1, wherein the one or more modifications include base substitutions to reflect all possible bases or combinations of bases at the one or more modified positions.

6. The method of claim 1, wherein the majority or all of the individual positions in the first key or the data set are individually substituted to create the set of modified first keys.

7. The method of claim 6, wherein the substitutions are adjacent substitutions.

8. The method of claim 6, wherein the substitutions are overlapping substitutions.

9. The method of claim 6, wherein the substitutions are non-adjacent substitutions.

10. The method of claim 1, wherein the one or more modifications are additions or deletion of positions in the key.

11. The method of claim 10, wherein the positions are modified individually.

12. The method of claim 1, wherein modifying the first key includes:
reordering the sequence of bases in the first key relative to an order of the bases occurring in the related oligomer sequences, wherein bases in the reference keys of the reference index are reordered relative to an order in the reference sequence.

13. A method of oligomer sequence mapping, comprising:
receiving data sets of sequences, each data set of related oligomer sequences obtained from a same fragment of genetic material;
receiving a key pattern corresponding to a reference index;
receiving the reference index, the reference index generated by respectively applying the key pattern to each of a plurality of locations of a reference sequence to obtain a plurality of reference keys, the application of the key pattern to each of the locations selecting a same number of specified positions of the reference sequence, wherein the reference index includes the reference keys ordered by bases at one or more positions in the reference keys, the reference keys of the reference index being a same length;
applying the key pattern to the oligomer sequences in each data set to generate keys comprising selected positions of the oligomer sequences of the data sets;
modifying individual positions of at least a portion of the keys to create a first set of modified keys;
modifying two or more combined positions of at least a portion of the keys to create a second set of modified keys; and
comparing the first and second set of modified keys to the reference index to determine one or more candidate locations of the oligomer sequences in the reference sequence, wherein the method is performed with a computer.

14. The method of claim 13, further comprising:
validating candidate locations for a first data set by comparing all bases of the first data set to indicated portions of the reference sequence corresponding to one or more reference keys matching to one or more first keys of the first data set.

15. The method of claim 13, wherein the modifications of the individual positions reflect all possible bases or combinations thereof.

16. A method of oligomer sequence mapping, comprising:
receiving data sets of sequences, each data set of related oligomer sequences obtained from a same fragment of genetic material;
receiving a key pattern corresponding to a reference index;
receiving the reference index, the reference index generated by respectively applying the key pattern to each of a plurality of locations of a reference sequence to obtain a plurality of reference keys, the application of the key pattern to each of the locations selecting a same number of specified positions of the reference sequence, wherein the reference index includes the reference keys ordered by bases at one or more positions in the reference keys, the reference keys of the reference index being a same length;
applying the key pattern to the oligomer sequences in each data set to generate keys comprising selected positions of the oligomer sequences of the data sets;
modifying two or more combined positions of at least a portion of the keys to create a first set of modified keys;
modifying two or more combined positions of at least a portion of the keys to create a second set of modified keys; and
comparing the first and second set of modified keys to the reference index to determine one or more candidate locations of the oligomer sequences in the reference sequence, wherein the method is performed with a computer.

17. The method of claim 16, further comprising:
validating candidate locations for a first data set by comparing all bases of the first data set to indicated portions of the reference sequence corresponding to one or more reference keys matching to one or more first keys of the first data set.

18. An oligomer sequence mapping system comprising:
an interface configured to receive:
a data set of related oligomer sequences obtained from a same fragment of genetic material, and
a key pattern corresponding to a reference index,
a memory that stores the reference index, the reference index generated by respectively applying the key pattern to each of a plurality of locations of a reference sequence to obtain a plurality of reference keys, the application of the key pattern to each of the locations causing a selection of a same number of specified positions of the reference sequence relative to the respective location, wherein the reference index stores the reference keys ordered by bases at one or more positions in the reference keys, the reference keys of the reference index being a same length; and
a processor coupled to the interface and to the memory, wherein the processor is configured to:
apply the key pattern to information in the data set to generate a first key comprising selected positions of the oligomer sequences;
modify one or more bases at one or more positions within the first key to create a set of one or more modified first keys, and
compare the first keys generated from the data set and the modified first keys to the reference keys in the reference index to identify one or more reference keys that match to one or more of the modified first keys, thereby determining one or more candidate locations of the oligomer sequences in the reference sequence, wherein the comparing uses the ordering of the reference keys in the reference index.

19. The system of claim 18, wherein the processor is further configured to validate the candidate locations by comparing bases of the data set to the indicated portions of the reference sequence corresponding to the matching reference keys.

20. The system of claim 18, wherein the processor is further configured to output locations of the oligomer sequences in the reference sequence.

21. The system of claim 18, wherein the processor is configured to perform multiple modification regimes using the data set.

22. The product of claim 18, wherein individual positions are modified.

23. The product of claim 18, wherein two or more combined positions are modified.

24. The system of claim 19, wherein the processor is configured to substitute the majority or all of the positions to create the set of modified first keys to reflect all possibilities of bases or combinations thereof.

25. A computer program product for oligomer sequence mapping, the computer program product being embodied in a non-transitory computer readable medium and comprising computer instructions for:

receiving a data set of related oligomer sequences obtained from a same fragment of genetic material;

receiving a key pattern corresponding to a reference index;

receiving the reference index, the reference index generated by respectively applying the key pattern to each of a plurality of locations of a reference sequence to obtain a plurality of reference keys, the application of the key pattern to each of the locations selecting a same number of specified positions of the reference sequence, wherein the reference index includes the reference keys ordered by bases at one or more positions in the reference keys, the reference keys of the reference index being a same length;

applying the key pattern to information in the data set to generate a first key comprising selected positions of the oligomer sequences;

modifying multiple positions within the first key to create a set of modified first keys; and comparing the modified first keys to the reference keys in the reference index to identify one or more reference keys that match to one or more of the modified first keys, thereby determining one or more candidate locations of the oligomer sequences in the reference sequence.

\* \* \* \* \*

UNITED STATES PATENT AND TRADEMARK OFFICE
CERTIFICATE OF CORRECTION

PATENT NO.       : 8,731,843 B2
APPLICATION NO.  : 12/698994
DATED            : May 20, 2014
INVENTOR(S)      : Aaron L. Halpern et al.

Page 1 of 1

It is certified that error appears in the above-identified patent and that said Letters Patent is hereby corrected as shown below:

In the Claims

In claim 10, column 86, line 66-67, delete "deletion" and insert --deletions-- so the lines read as "The method of claim 1, wherein the one or more modifications are additions or deletions of positions in the key"

Signed and Sealed this
Tenth Day of March, 2015

Michelle K. Lee
*Deputy Director of the United States Patent and Trademark Office*